US 11,364,034 B2

(12) United States Patent
Veeckmans et al.

(10) Patent No.: US 11,364,034 B2
(45) Date of Patent: Jun. 21, 2022

(54) METHOD AND APPARATUS FOR IMPROVED AIRFLOW DISTRIBUTION THROUGH GENERATION OF A COMPUTER MODEL OF A PATIENT'S LUNGS

(71) Applicants: MATERIALISE N.V., Leuven (BE); FLUIDDA NV, Kontich (BE)

(72) Inventors: Bart Veeckmans, Leuven (BE); Koen Engelborghs, Leuven (BE); Jan De Backer, Leuven (BE); Wim Vos, Leuven (BE)

(73) Assignee: Materialise N.V., Leuven (BE)

( * ) Notice: Subject to any disclaimer, the term of this patent is extended or adjusted under 35 U.S.C. 154(b) by 238 days.

(21) Appl. No.: 15/776,326

(22) PCT Filed: Nov. 30, 2016

(86) PCT No.: PCT/US2016/064181
§ 371 (c)(1),
(2) Date: May 15, 2018

(87) PCT Pub. No.: WO2017/095901
PCT Pub. Date: Jun. 8, 2017

(65) Prior Publication Data
US 2018/0325525 A1    Nov. 15, 2018

Related U.S. Application Data

(60) Provisional application No. 62/261,300, filed on Nov. 30, 2015.

(51) Int. Cl.
*A61F 2/02* (2006.01)
*A61B 5/08* (2006.01)
(Continued)

(52) U.S. Cl.
CPC .......... *A61B 17/12104* (2013.01); *A61B 5/08* (2013.01); *A61B 17/12036* (2013.01);
(Continued)

(58) Field of Classification Search
CPC ........ A61B 17/12104; A61B 17/12109; A61B 17/12113; A61B 17/12122;
(Continued)

(56) References Cited

U.S. PATENT DOCUMENTS 9,795,388 B1 * 10/2017 Evans ................ A61B 17/1214
2001/0035183 A1 * 11/2001 Sexton ................ A61B 5/0813
128/200.24

(Continued)

FOREIGN PATENT DOCUMENTS

JP    2005505355 A    2/2005
WO   2007111207 A1   10/2007
(Continued)

OTHER PUBLICATIONS

Supplementary International Search Report dated Nov. 30, 2017 in corresponding application PCT/US2016/064181.
(Continued)

*Primary Examiner* — Joseph D. Boecker
*Assistant Examiner* — Brian T Khong
(74) *Attorney, Agent, or Firm* — Patterson + Sheridan, LLP

(57) ABSTRACT

Methods and devices for improving airflow distribution in treatment of respiratory conditions are disclosed. According to various embodiments, blocking devices may be used to redirect air away from healthy portions of the lung to diseased portions so that inhaled medication may be more effectively delivered to the patient.

24 Claims, 18 Drawing Sheets

(51) Int. Cl.

| | |
|---|---|
| *G16H 50/50* | (2018.01) |
| *A61F 2/82* | (2013.01) |
| *G16H 30/40* | (2018.01) |
| *A61B 5/055* | (2006.01) |
| *A61B 5/087* | (2006.01) |
| *A61F 2/04* | (2013.01) |
| *A61B 17/12* | (2006.01) |
| *A61M 16/04* | (2006.01) |
| *A61M 16/00* | (2006.01) |
| *G16H 20/40* | (2018.01) |
| *A61M 15/00* | (2006.01) |

(52) U.S. Cl.
CPC .......... *A61B 17/12172* (2013.01); *A61F 2/02* (2013.01); *A61F 2/82* (2013.01); *A61M 16/022* (2017.08); *A61M 16/0406* (2014.02); *G16H 20/40* (2018.01); *G16H 30/40* (2018.01); *G16H 50/50* (2018.01); *A61B 5/055* (2013.01); *A61B 5/087* (2013.01); *A61B 2576/02* (2013.01); *A61F 2002/043* (2013.01); *A61F 2220/0008* (2013.01); *A61F 2250/001* (2013.01); *A61F 2250/0002* (2013.01); *A61F 2250/0039* (2013.01); *A61F 2250/0063* (2013.01); *A61F 2250/0067* (2013.01); *A61M 15/00* (2013.01); *A61M 2207/00* (2013.01)

(58) Field of Classification Search
CPC ........ A61B 17/12099; A61B 17/12131; A61B 17/12145; A61B 17/12172; A61B 2017/1205; A61B 2017/00526; A61B 5/087; A61B 5/085; A61B 5/091; A61B 5/055; A61B 5/0555; A61B 2576/00; A61B 2576/02; A61M 16/0406; A61M 16/0404; A61M 16/0402; A61M 16/04; A61M 16/042; A61M 16/022; A61M 16/021; A61M 16/024; A61M 16/026; G16H 50/00; G16H 50/20; G16H 50/50; G16H 50/70; A61F 2/04; A61F 2/02; A61F 2/82; A61F 2002/043
See application file for complete search history.

(56) References Cited

U.S. PATENT DOCUMENTS

| | | | |
|---|---|---|---|
| 2003/0070682 A1* | 4/2003 | Wilson ................. | A61F 2/2412 128/207.16 |
| 2003/0228344 A1* | 12/2003 | Fields ................... | A61F 2/04 424/423 |
| 2004/0055606 A1* | 3/2004 | Hendricksen .... | A61B 17/12022 128/207.14 |
| 2004/0060563 A1* | 4/2004 | Rapacki ........... | A61B 17/12022 128/207.14 |
| 2005/0016530 A1* | 1/2005 | McCutcheon ... | A61B 17/12159 128/200.24 |
| 2005/0056292 A1* | 3/2005 | Cooper ............. | A61B 18/1492 128/898 |
| 2005/0178389 A1* | 8/2005 | Shaw ............... | A61B 17/12104 128/207.15 |
| 2006/0116749 A1* | 6/2006 | Willink ............. | A61M 25/0084 623/1.11 |
| 2006/0264772 A1* | 11/2006 | Aljuri .................. | A61B 5/7278 600/538 |
| 2008/0058633 A1* | 3/2008 | Boyden ................. | G16H 50/50 600/407 |
| 2012/0072193 A1* | 3/2012 | De Backer ............. | G16H 50/50 703/2 |
| 2014/0088698 A1 | 3/2014 | Roels et al. | |
| 2014/0142455 A1* | 5/2014 | Freitag ............... | A61B 1/00082 600/538 |
| 2014/0324094 A1 | 10/2014 | Weber et al. | |
| 2015/0265799 A1 | 9/2015 | Smith et al. | |
| 2016/0055264 A1* | 2/2016 | Meadows .............. | A61L 27/14 703/9 |

FOREIGN PATENT DOCUMENTS

| | | | | |
|---|---|---|---|---|
| WO | 2014125059 A1 | 8/2014 | | |
| WO | WO-2014125059 A1 * | 8/2014 | ............... | A61B 6/50 |

OTHER PUBLICATIONS

International Search Report dated Mar. 10, 2017 in corresponding application PCT/US2016/064181.
Werbeneth, et al., Choosing MEMs Pressure Sensors for Medical Device Applications, 2014, Medical Design Briefs, https://www.medicaldesignbriefs.com/component/content/article/mdb/articles/20907.

* cited by examiner

METHOD AND APPARATUS FOR IMPROVED AIRFLOW DISTRIBUTION THROUGH GENERATION OF A COMPUTER MODEL OF A PATIENT'S LUNGS

CROSS-REFERENCE TO RELATED APPLICATIONS

This application claims the benefit of U.S. Provisional Patent No. 62/261,300, filed Nov. 30, 2015. The content of the provisional application is hereby incorporated by reference in its entirety.

BACKGROUND OF THE INVENTION

Field of the Invention

This application relates to treatment of respiratory conditions. In particular, this application relates to methods and devices which allow for controlling airflow distribution in a lung of a patient's respiratory system.

Description of the Related Technology

Currently, patients with respiratory conditions, such as chronic obstructive pulmonary disease (COPD), idiopathic pulmonary fibrosis (IPF), asthma, and cystic fibrosis (CF), are often treated by administering drugs which are inhaled by the patient into their lungs. The inhaled drugs are typically provided in a powder form, and patients inhale them so that the drug reaches the affected portions of the lung. Sometimes, lung disorders are localized such that certain portions of a lung are healthy, and other portions of the lung are diseased. When administering inhaled drugs for treatment of localized lung disorders, the diseased portions of the lung often have decreased ventilation. Because the disease portions of the lung often have decreased ventilation, the inhaled drugs tend to be primarily delivered to the healthy portions having better ventilation. As a result, diseased regions can remain untreated or under-treated. In some instances, patients are directed to lay on their side in order to create better ventilation patterns for treating localized lung disorders using inhaled drugs. However, patient positioning has significant limitations. Endoscopic procedures can also be used to deliver drugs to diseased areas, but these procedures tend to be invasive and expensive. Other treatments such as lung volume reduction and selective lung volume ablation also have been employed to treat respiratory conditions. Although these techniques can alter the lung tissue to alleviate some symptoms of the disease, they do not improve drug delivery to diseased areas.

DETAILED DESCRIPTION OF CERTAIN INVENTIVE EMBODIMENTS

Figure 1:
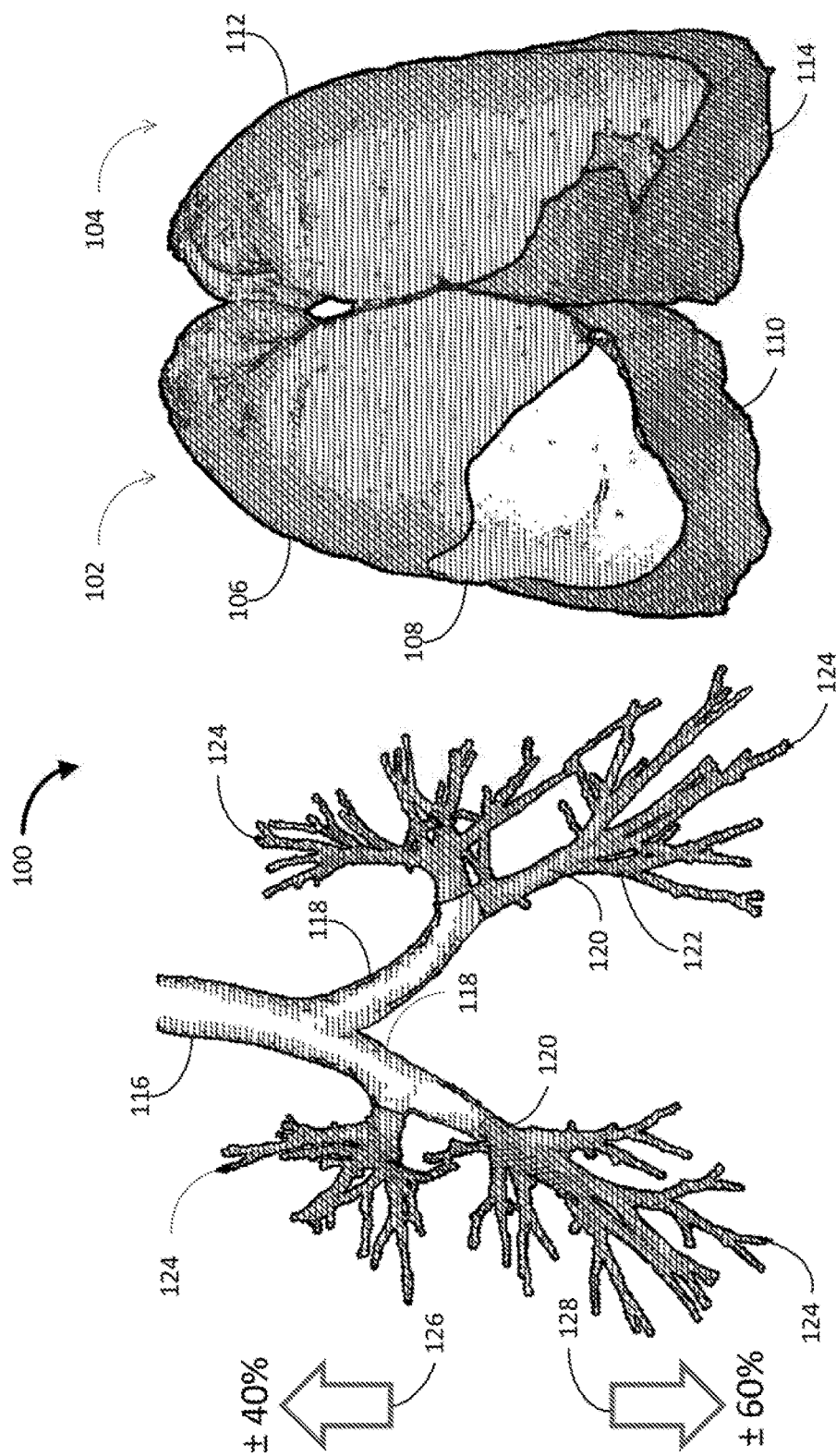
FIG. 1 is an example of a healthy respiratory system.

Embodiments disclosed herein relate to methods and devices which can be used for the treatment of patients who suffer from respiratory conditions. These respiratory conditions may include COPD, IPF, asthma and CF, but a person skilled in the art will readily recognize that they equally apply to other conditions.

Embodiments disclosed herein relate to methods and devices which can be used to optimize airflow distribution for an individual patient by obstructing, partially obstructing, or temporarily obstructing airway passages in the lungs. Many respiratory conditions are characterized by regional inhomogeneity in the disease expression. Put more simply, many respiratory conditions result in certain parts of the lung remaining healthy, while other parts of the lung become diseased and do not work as well. In these types of respiratory conditions, the treatments utilizing inhaled drugs do not always lead to acceptable results. This is because as a portion of the lung becomes more and more diseased, it suffers from decreasing ventilation. Inhaled drugs are delivered using the airflow within the lung. Thus, diseased parts of the lungs with reduced ventilation do not receive the medicine that they need in order to heal properly. Instead, most of the inhaled medication flows toward the healthy parts of the lungs, which are not in need of treatment. The inventors of this application have recognized this conundrum. When parts of the lung become diseased, those parts typically have decreased ventilation. Because they have decreased ventilation, it is more difficult to reach them with inhaled treatment.

Current treatments for these types of diseases typically involve altering the lung tissue. For example, a lung-volume-reduction ("LVR") surgery may be performed in which unhealthy portions of the lung tissue are removed so that the remaining tissue is healthy and the lung as a whole is made more functional. Although LVR can improve breathing and lung capacity, it has several drawbacks. First, because it is a surgical procedure, it can be invasive and require lengthy and expensive hospital stays. Second, LVR can lead to air leakage in the lungs, increased risk of pneumonia or infection, or other significant risks generally present in surgical procedures.

Other treatments for localized lung disease involve the use of ablation. In these treatment methods, airways are opened using mild heat to reduce excess smooth muscle tissue in the airways of the lung. The removal of this muscle tissue can allow patients to breathe more easily, but drug delivery to any remaining diseased areas is difficult. In still other lung-disease indications such as emphysema, for example, the use of minimally invasive coil implants is being studied. These coil implants are intended to help mitigate the breathing problems caused by the loss of the elastic properties in the lung. Although these treatments can slow the progression of these diseases, they do not improve delivery of inhaled drugs to diseased areas having decreased ventilation.

Still other treatments include the placement of silicone or metal airway stents, which are devices designed to keep tubular structures open and stable. These devices are typically placed using bronchoscopes and delivery catheters. Whereas many patients experience an immediate improvement, airway stents also suffer from shortcomings. Over time, metal stents may be incorporated into the airway wall and become covered with mucosa. If stents are chosen too small, they may migrate. If they are chosen too large, they may not open after delivery or may cause stress on the airway wall. Even though opening the passage to a diseased area helps to administer drugs, it does not prevent delivery of considerable doses of drugs to healthy areas of the lungs. As a result, current treatment methods provide little hope for reversing chronic lung disease.

The inventors have devised a new and innovative treatment approach. At its highest level, the treatment approach involves simulating the airflow through the airway passages in a patient's respiratory system. Using the information provided by the simulated airflow model, the patient can be treated either by redirecting the airflow, or by locally administering drugs using drug-delivery devices, such as drug-eluting devices or nebulizers, or a combination of both. Ventilation or airflow through the air passages of the lungs can be simulated using techniques such as functional respiratory imaging. Functional respiratory imaging ("FRI") allows a pulmonologist to assess the state of lung disease by creating patient-specific lung models starting from three-dimensional imaging of the respiratory system. Airflow through the lung, including the structural behavior of airway passages, can be modeled using techniques such as FRI.

With the information provided by the simulation, various treatment approaches can be implemented in which airflow is redirected within the lungs to improve lung function. In some embodiments, the airflow can be redirected to promote airflow toward diseased regions of the lung. In these embodiments, the efficacy of an inhaled drug may be improved because it can be redirected toward diseased regions more in need of the inhaled therapy. In other embodiments, airflow may be redirected away from diseased regions. In these embodiments, airflow may be redirected toward healthy regions in order to stimulate those regions into improved lung function.

Airflow within the lungs can be redirected using blocking devices. In general, the blocking devices may have an outer shape that fits the airway passage (thereby creating a tight and substantially airproof fit). These devices may also include an inner shape or diameter that determines a degree or level of narrowing or blocking of an airway passage. In certain embodiments, the inner shape of the device can be static or fixed. In these embodiments, the interior of the device provides the same level of narrowing at all times. The blocking devices can also have an inner shape that is able to transition. More specifically, the inner shape may be able to open and close in response to external stimuli so that air is permitted to pass through the device while in an open position, and air is obstructed (either partially or fully) when in a narrowed configuration.

The blocking devices may also allow for a gradual transition in which the opening and closing of the inner channel can be externally controlled using electronic signals. In these implementations, the inner shape may include a microelectromechanical system (MEMS) which is controllable using radio signals. The MEMS device may be able to open partially, open fully, or close completely according to the therapeutic need. In these transitioning blocking devices, the airflow can be redirected temporarily during treatment, while an inhaled drug is administered.

In some embodiments, the outer portion of a blocking device may function as a docking station, which allows for the inner shape to be exchanged without removing or otherwise disturbing the device after it has been implanted in the airway passage. Thus, a static inner shape may be used in a docking station configuration such that it initially is open, but later is modified by replacing the static inner part with a differently configured inner part.

The blocking devices themselves may take various forms. In general, the blocking devices may be placed and/or removed using a non-surgical interventional approach. The blocking devices may be off-the-shelf devices which are selected based on their size and narrowing features. The blocking devices may also be off-the-shelf devices which are selected from a library of devices. In some embodiments, the off-the-shelf devices may be selected based on having an optimal combination of outer and inner shape which is selected from a size and shape library.

The blocking devices may also be patient-specific devices. The patient-specific devices may be created using additive manufacturing techniques. In these implementations, the outer shape may be designed specifically based on the anatomy of the airway passage. By designing the outer shape based on the specific anatomy of the airway passage, a better fit may be achieved when the blocking device is placed in vivo. The patient-specific blocking devices may also provide a docking-station configuration such that the inner shape can be exchangeable without removing the body structure of the blocking device. In addition, the inner shape of the blocking device may also be patient specific to provide a desired level of narrowing of the airway passage.

In sum, the methods and devices disclosed herein allow for local administration of drugs through drug-delivery systems, such as drug-eluting devices, and for directing and/or redirecting inhaled drugs to specific parts of the lung based on therapeutic needs. In particular, by redirecting the airflow using the blocking devices disclosed herein, inhaled drugs can be directed toward diseased regions of the lung so that those regions may be treated and possibly healed, thereby avoiding the need for removing or otherwise modifying lung tissue.

Turning now to FIG. 1, an anterior view of a normal, healthy respiratory system 100 is shown. On the left side, the airway passages through the lungs are shown, while on the right side the lungs themselves are shown. The respiratory system 100 includes a right lung 102 and a left lung 104. The right lung includes a right lung upper lobe 106, a right lung middle lobe 108, and a lower lobe of the right lung 110. The left lung 104 has only two lobes, the upper lobe 112 and the lower lobe 114. Turning to the left side of FIG. 1, the airway passages of the respiratory system 100 are shown. These airway passages pass through the lung tissue of the right lung 102 and the left lung 104. The airway passages include a trachea 116 (also commonly referred to as a windpipe). The trachea 116 extends from the chest area towards the head of the patient, and allows air to be inhaled and exhaled through the mouth and nose of the patient. As the trachea 116 extends downward, it divides into two branches 118. These two branches are commonly referred to as bronchi. As shown, there is a main (right) bronchus 118 which extends downward from the trachea and to the left side of the drawing (because the view is from the anterior, or front, of the body). The main (right) bronchus 118 provides an airway passage into the right lung 102. There is also a main (left) bronchus 118 on the left side of the trachea (right side in the drawing) which leads into the left lung 104.

The airway passages of the respiratory system 100 grow progressively smaller as they branch out within the lungs until they ultimately become microscopic in size. The main bronchi 118 branch into lobar bronchi 120. Although each main bronchus 118 branches into two lobar bronchi 120, only one is marked in each branch. The lobar bronchi 120 in turn, narrow into segmental bronchi 122 which carry air further down the air passages to bronchioles 124. The bronchioles 124 terminate as terminating bronchioles. At the end of the bronchioles, there are clusters of microscopic air sacs called alveoli (not shown). In the alveoli, oxygen from the air is absorbed into the blood. Carbon dioxide, a waste product of metabolism, travels from the blood to the alveoli, where it can be exhaled upward through the airway passages of the lungs.

In the example shown in FIG. 1, the respiratory system 100 shown is generally healthy. In a generally healthy respiratory system such as respiratory system 100, the typical ventilation pattern has been shown to be 40% of the air going to the upper lobes, while 60% of the inhaled air goes to lower lobes. In FIG. 1, an arrow 126 indicates the ventilation to the upper lobes, while arrow 128 indicates ventilation to the lower lobes. In this example of a healthy lung, the ventilation pattern is 40% of inhaled air going to upper lobes while approximately 60% of inhaled air travels to lower lobes.

Figure 2:
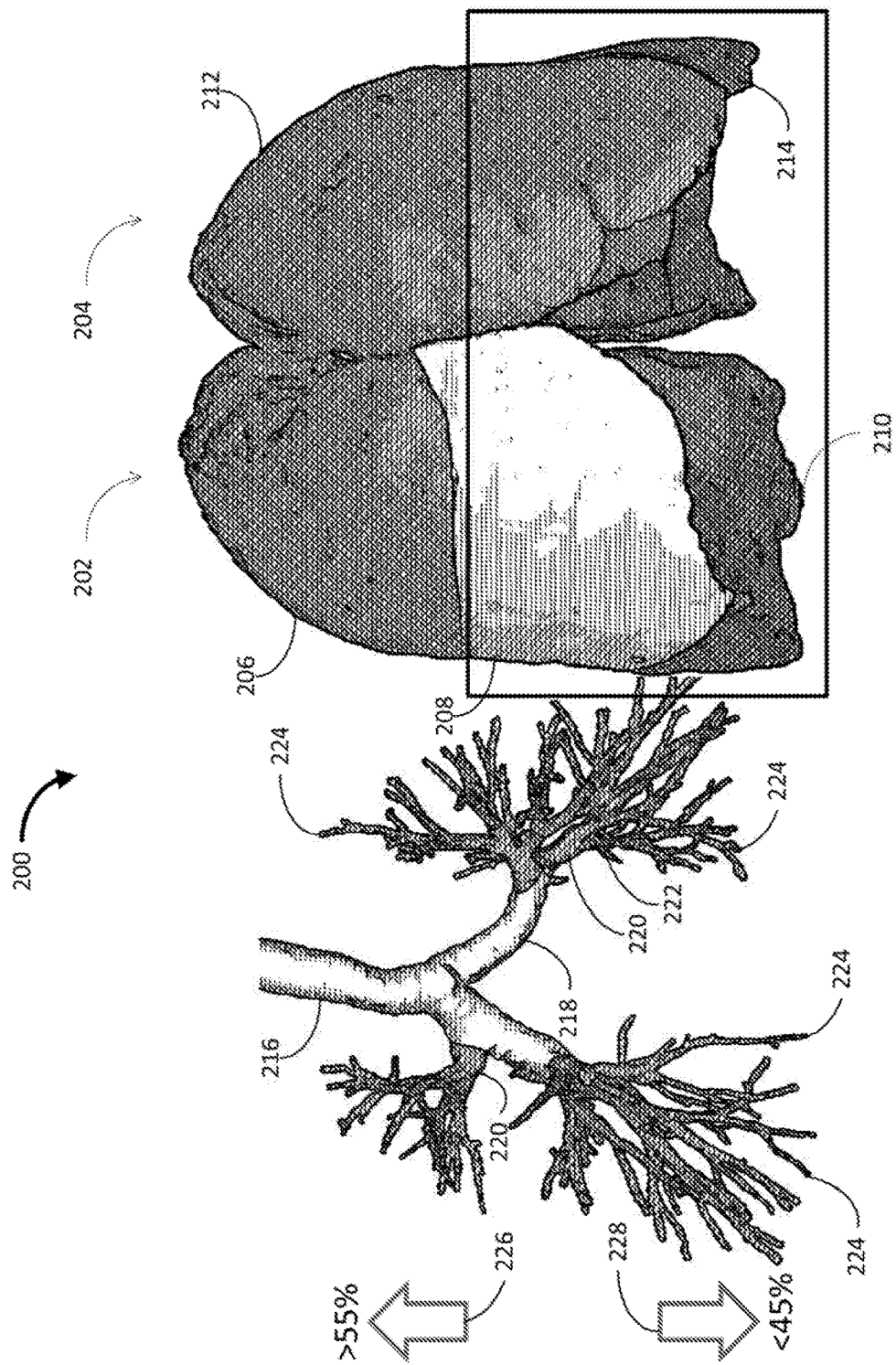
FIG. 2 is an example of a respiratory system having inflammation in the lower lobes.

As noted above, embodiments of the invention relate to improving treatment of diseased lungs and respiratory systems. FIG. 2 provides one example of a diseased respiratory system 200. In this case, the respiratory system 200 suffers from inflammation in the lower lobes. As shown, the diseased respiratory system 200 includes right lung 202 and left lung 204. The right lung 202 has an upper lobe 206, a middle lobe 208 and a lower lobe 210. The respiratory system 200 also includes a left lung upper lobe 212 and a left lung lower lobe 214. As can be seen by comparing the example of the healthy lung from FIG. 1 with the diseased lungs from FIG. 2, the lower portion of the diseased lung, including middle lobe 208, is larger than that of the healthy lung from FIG. 1.

FIG. 2 also shows the airway passages associated with the diseased respiratory system 200. The airway passages include the trachea 216 and the main left and right bronchi 218. The main bronchi 218 branch into lobar bronchi 220 which begin to show signs of the inflammation, especially the lobar bronchi associated with the middle and lower lobes 208, 210 and 214 respectively. The segmental bronchi 222 also are shown in the inflamed respiratory system of FIG. 2. The segmental bronchi branch into bronchioles 224. Although not readily apparent from the drawing, the inflammation in the lower portion of the lung may also impact the airway passages shown in FIG. 2. In particular, the passageways may be narrowed due to the inflammation thereby preventing the free-flowing of air through the passages. Due to the inflammation in the lower portion of the respiratory system 200, the ventilation pattern in this unhealthy respiratory system 200 is not the typical pattern of 40% of inhaled air reaching the upper lobes and 60% of inhaled air reaching the lower lobe.

The upper lobe ventilation in this example, denoted by upward pointing arrow 226 indicates that more of the airflow enters the upper lobes of the lung because they are healthier than the lower lobes. In particular, the upper lobes receive 55% or more of the inhaled air. The ventilation pattern shown in FIG. 2 also demonstrates how the inflamed portion of the lung, due to its impaired function, does not receive the normal amount of airflow. As shown by the arrow 228, less than 45% of the inhaled air reaches the lower portion of the respiratory system 200. Because of this reduced airflow, when inhaled treatments are administered to the respiratory system 200, most of the treatment ends up reaching the healthy portion of the lung—the portion of the lung less in need of treatment. Conversely, the inflamed lower lobes of the lung receive less than 45% of the inhaled medication. Thus, the inflamed portions of the lung, which would benefit from the medication, receive insufficient doses due to the ventilation pattern that manifests itself as a result of the disease.

Figure 3:
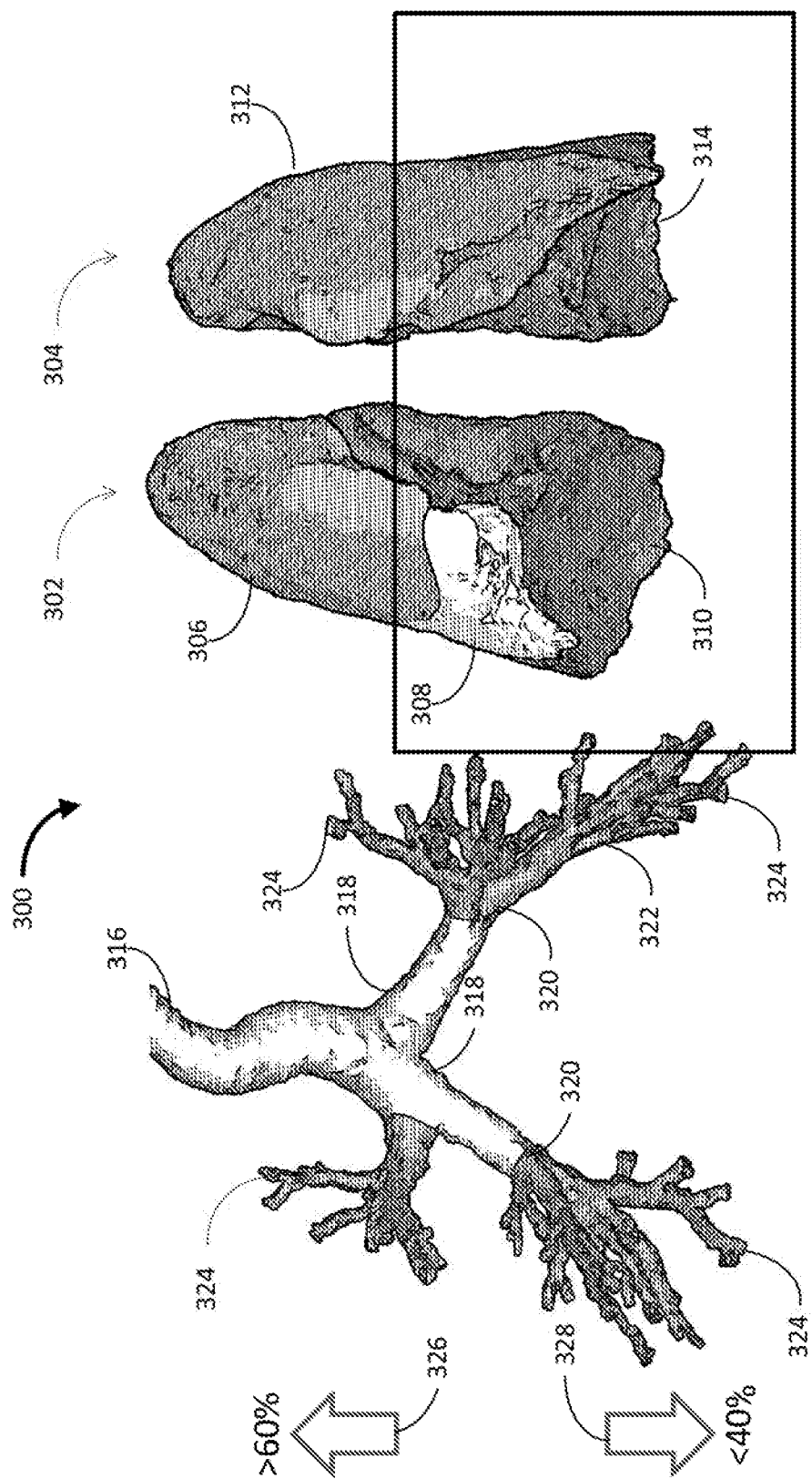
FIG. 3 is an example of a respiratory system suffering from fibrosis in the lower and middle lobes of the lungs.

Turning now to FIG. 3, an example of the respiratory system 300 suffering from fibrosis is shown. The respiratory system includes a right lung 302 and a left lung 304. The right lung 302 includes an upper lobe 306, a middle lobe 308 and a lower lobe 310. The left lung 304 also includes an upper lobe 312 and a lower lobe 314. The middle lobe 308 and the lower lobes 310 and 314 may include scar tissue which is formed as a result of the fibrosis. The fibrotic respiratory system 300 also may include symptoms in the airway passages. Here airway passages include a trachea 316 which branches into a left bronchus 318 and a right bronchus 318, respectively. The main bronchi 318 in each of the left and right lungs further branch into lobar bronchi 320. However, due to the scarring of tissue caused by the fibrosis, the recoil of the airway passages may be reduced. The lobar bronchi 320 branch into segmental bronchi 322, which in turn divide into bronchioles 324. FIG. 3 also provides an example of a typical ventilation pattern in a fibrotic respiratory system such as respiratory system 300. As indicated by up arrow 326, in a respiratory system 300 having fibrosis in the middle and lower lobes, more than 60% of inhaled air is directed to the upper respiratory system. The diseased portion, as indicated by downward facing arrow 328, receives only 40% of the inhaled air. As a result of this ventilation pattern, treatment of the fibrotic portions of the lungs using inhaled medication is problematic, as most of the medication reaches the healthy upper portions.

Figure 4:
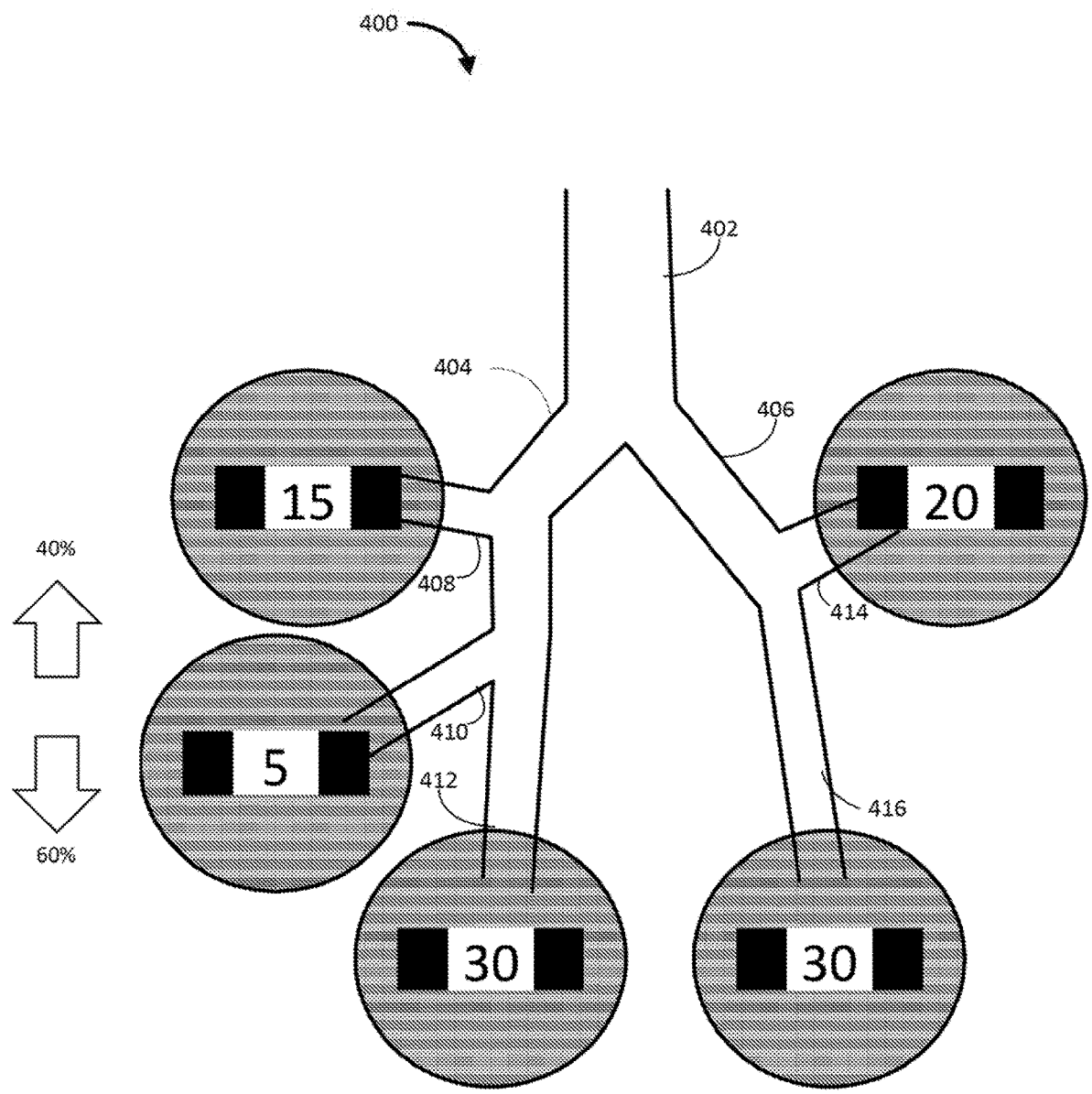
FIG. 4 is an example of airflow distribution through airway passages in a healthy lung such as the lung shown in FIG. 1.

As discussed above, embodiments of the invention relate to creating obstructions within the airway passages in order to redirect airflow within those airway passages. FIG. 4 is a simplified schematic example of airflow distribution 400 through airway passages in a healthy respiratory system such as respiratory system 100 shown in FIG. 1. As will be discussed in more detail below, these values may be obtained in various ways, including, for example, by means of functional respiratory imaging.

In this example, the airway passages include the trachea 402. The trachea branches into a right main bronchus 404 and a left main bronchus 406. The right main bronchus 404 branches into three lobar bronchi, each of which extends into one of the lobes of the right lung. The lobar bronchus 408 extends into the upper lobe of the right lung. The middle lobe bronchus 410 extends into the middle lobe of the right lung, and the lower lobe bronchus 412 extends to the lower lobe of the right lung. Similarly, the lobar bronchus 414 extends into the upper lobe of the left lung. Lobar bronchus 416 extends into the lower lobe of the left lung.

FIG. 4 includes ventilation percentage values which relate to each of the lobar bronchi shown. For example, the lobar bronchus 408 extending into the upper lobe of the right lung has a ventilation value of 15%. This means that 15% of the airflow travels into this lobar bronchus 408. The lobar bronchus 410 associated with the middle lobe of the right lung has a ventilation value of 5%, while the lobar bronchus 412 associated with the right lower lobe receives 30% of the airflow as shown in the figure. As noted above, the left main bronchus 406 branches into to lobar bronchi 414 and 416. The lobar bronchus 414 extends into the upper lobe of the left lung. As shown, this segment receives 20% of the airflow. The lobar bronchus 416 associated with the lower lobe of the left lung receives 30% of the airflow. Taken together, the two lobar bronchi 412, 416 associated with lower lobes receive 60% of the airflow into the respiratory system. This value is consistent with the value shown in FIG. 1 above. The remaining lobes—namely the middle lobe of the right lung, the upper lobe of the right lung, and the upper lobe of the left lung—collectively receive 40% of the inhaled airflow, also consistent with the ventilation pattern shown above in connection with FIG. 1.

Figure 5A:
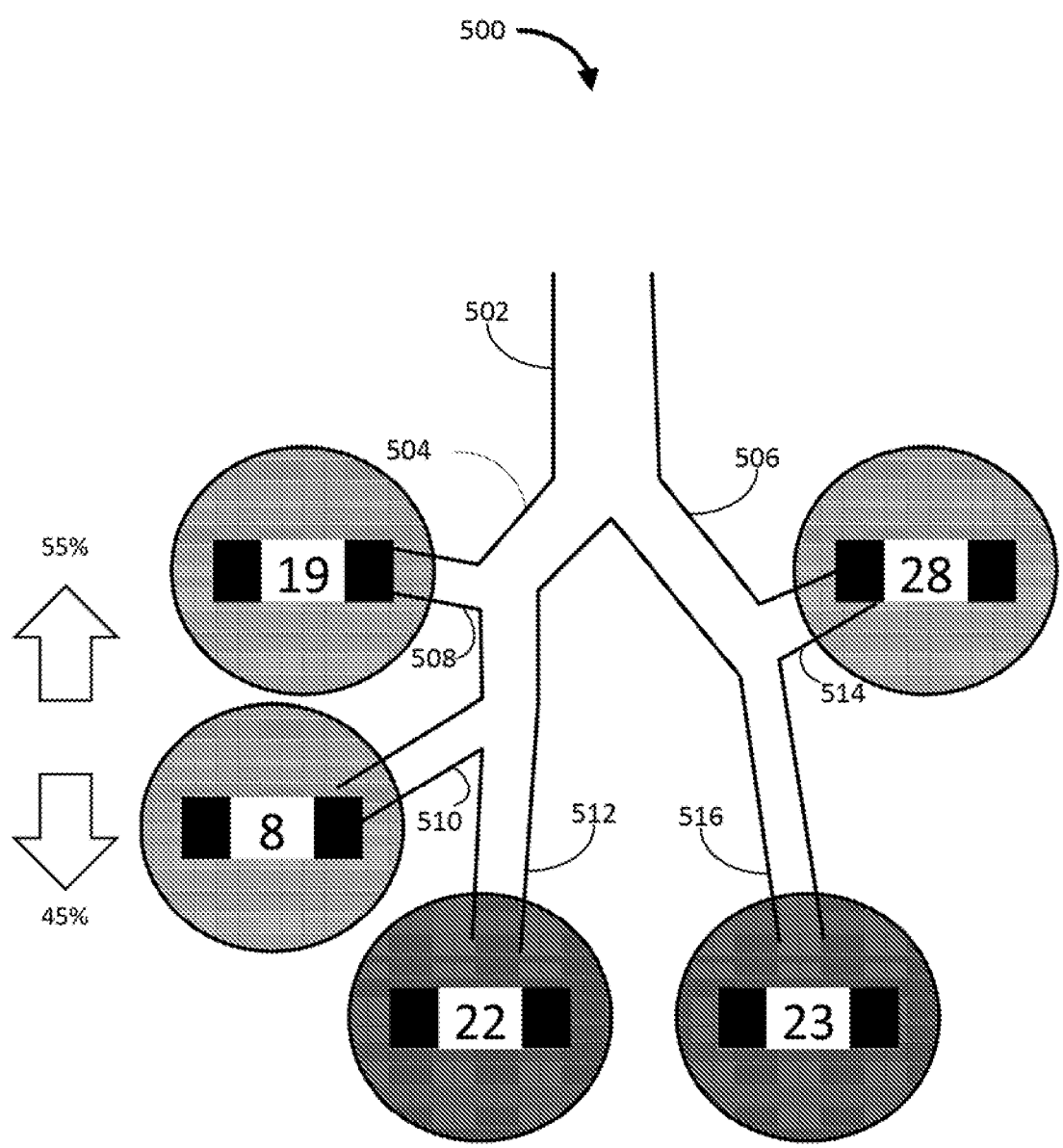
FIG. 5A is an example of an airflow distribution through airway passages in diseased lungs such as those shown in FIGS. 2-3.
Figure 5B:
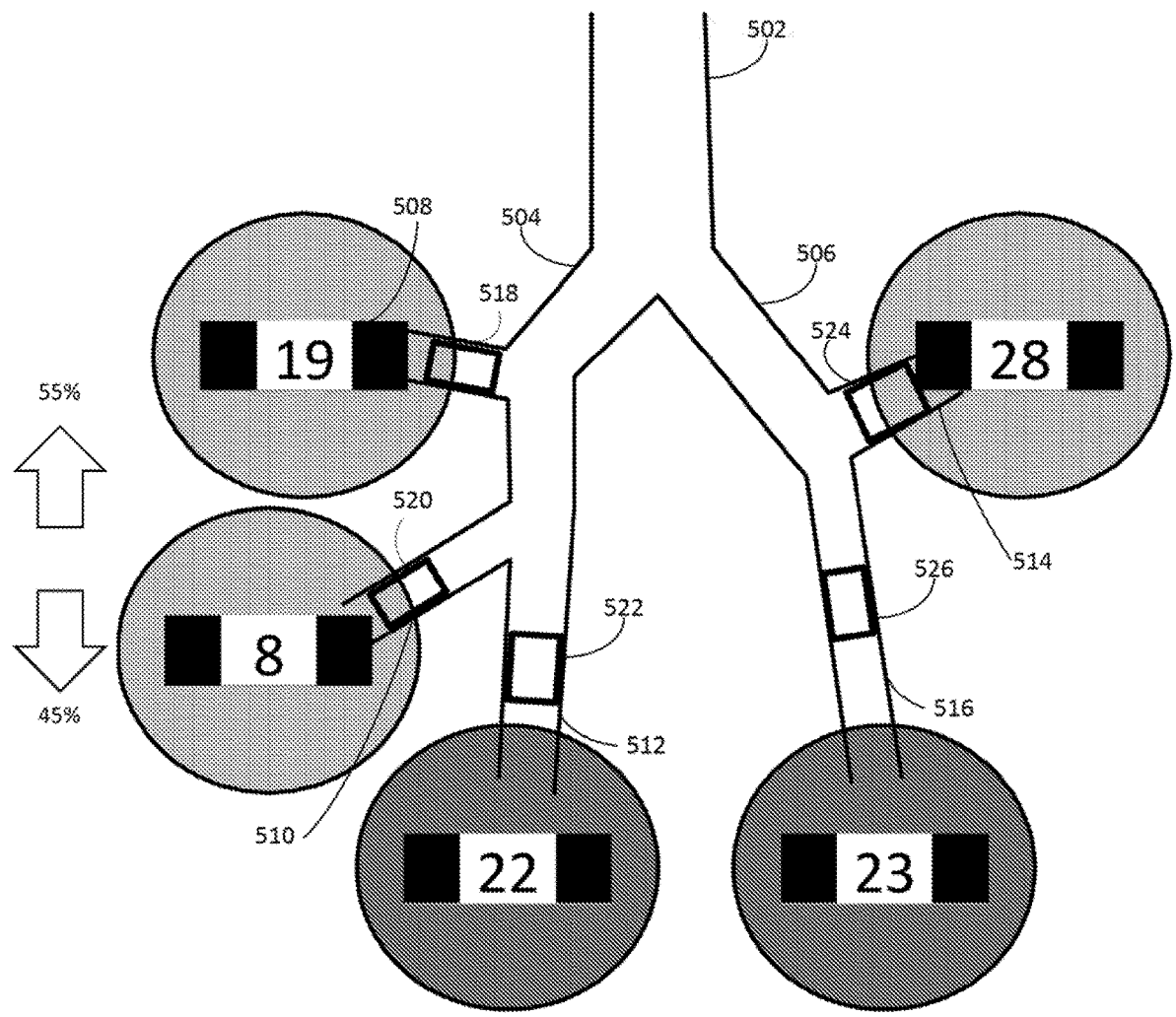
FIG. 5B provides an illustration of possible placement locations for airway obstructions in the airway passages shown in FIG. 5A.

In the respiratory system schematic shown in FIG. 4, the lung is healthy and has a normal ventilation pattern. As a result, there is typically no need to modify the airflow within the lung. However, in the case of diseased lungs, the ventilation patterns may not be optimal, and airflow may need to be redirected in order to deliver medical treatment effectively. FIGS. 5A-5B are examples of airflow distributions through airway passages in diseased lungs such as, for example, those shown in FIG. 2 and FIG. 3 above.

FIG. 5A shows a simplified representation of a ventilation pattern 500 of a respiratory system. In this particular example, the ventilation pattern is one measured in a diseased respiratory system such as respiratory system 200 discussed above in connection with FIG. 2. Like FIG. 4, these ventilation percentage values may be obtained using FRI or some other suitable measurement technique. The ventilation pattern 500 is shown in relation with the airway-passage anatomy which includes a trachea 502. The trachea 502 branches into the main (right) bronchus 504 and the main (left) bronchus 506. The main (right) bronchus 504 branches to three lobar segments—each associated with one of the lobes of the right lung. Lobar segment 508 extends into the upper lobe of the right lung. As indicated in the figure, in the ventilation pattern 500 of this diseased lung, 19% of the inhaled air goes to the airway passage associated with lobar segment 508. Lobar segment 510, associated with the middle lobe of the right lung, receives 8% of the airflow entering the respiratory system. Lobar segment 512, which extends downward to the right lower lobe of the respiratory system, carries 22% of the inhaled air into that portion of the lung area of the respiratory system.

The main (left) bronchus 506, which extends into the left lung, branches into lobar segments 514 and 516. Lobar segment 514 extends into the upper lobe of the left lung. As shown in the figure, according to the ventilation pattern 500, 28% of the inhaled air is directed to lobar segment 514. The other branch extending from the main (left) bronchus 506 is the lobar segment 516, which extends into the lower (diseased) lobe of the left lung. As shown, 23% of the airflow travels through this segment. Taken together, the percentage of airflow reaching the lower lobes in the ventilation pattern 500 is 45%, consistent with the values shown in connection with the inflamed respiratory system 200 shown above in FIG. 2. Similarly, adding the percentages associated with the middle and upper lobes shown in FIG. 5, the ventilation pattern 500 reveals that 55% of the airflow reaches the healthier middle and upper lobes in this particular respiratory system. Thus, the ventilation pattern 500 measured in FIG. 5A reveals that inadequate airflow is reaching the lower lobes of the respiratory system.

Turning now to FIG. 5B, the same simplified representation of the ventilation pattern shown in FIG. 5A is provided. Here, in accordance with certain embodiments of the invention, a series of blocking devices may be positioned within the airway passages in order to redirect airflow. For example, within lobar segment 508, a blocking device 518 is positioned within the segment. Typically, the blocking device may be positioned within the lobar segment near the main bronchus from which it extends. However, other locations within the airway may also be used. Lobar segment 510, which extends from the main bronchus into the middle lobe of the left lung also may receive a blocking device 520. Similarly, blocking devices such as blocking device 522, blocking device 524, and blocking device 526 may also be implanted into the lobar segments 512, 514, and 516 respectively. These blocking devices may be implanted using non-invasive implantation techniques typically used for implantation of bronchial stents.

When a patient presents with a diseased lung that requires treatment, the ventilation pattern 500 may provide useful information to the treating physician, which enables him or her to determine how to modify airflow within the airway passages to most effectively treat the patient. In some embodiments, airflow may be redirected within the airway passages to ensure that diseased portions of the lungs receive a higher percentage of the airflow. In these situations, an inhaled drug may have increased efficacy because more of the inhaled powder reaches those parts of the lungs actually needing treatment.

Figure 5C:
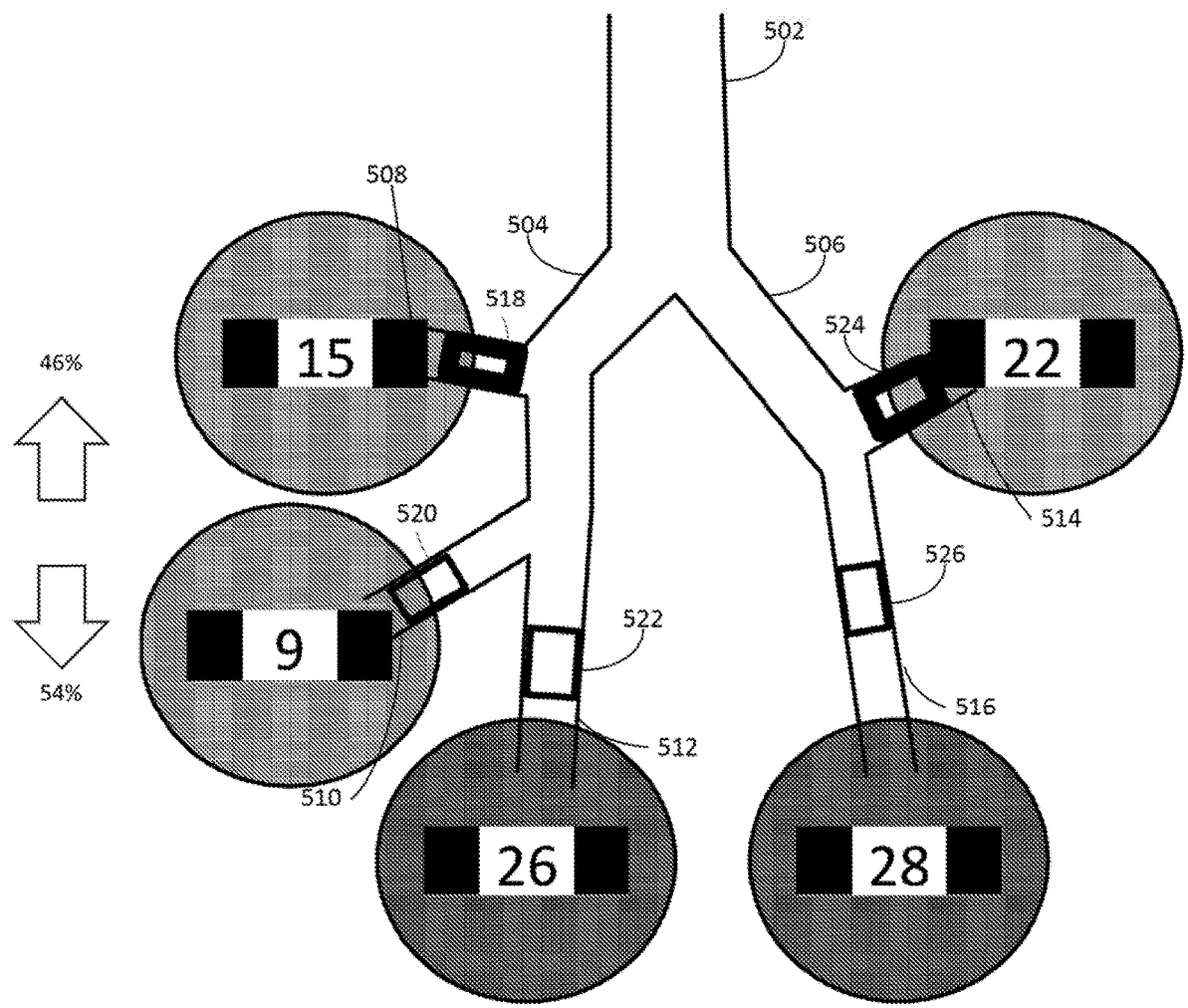
FIG. 5C provides an example of a modified airflow distribution in accordance with one or more embodiments disclosed herein.

FIG. 5C provides an example of a modified airflow distribution in which airway passages are narrowed using the blocking devices to modify the ventilation pattern 500 in such a way that increases the amount of air reaching the diseased lower lobes of the respiratory system. In this example, the blocking device 518 which has been positioned in lobar segment 508 is narrowed to obstruct airflow into the airway passage. As a result of the obstructed airway, the ventilation pattern 500 in this diseased lung changes. In particular, the percentage of inhaled air reaching the upper right lobe of the lung is reduced from 19% to 15%. The blocking device 524 placed in the lobar segment 514 also is narrowed to obstruct the airway passage to the upper lobe of the left lung. In this case, the airflow to the left upper lobe is reduced from 28% to 22%.

The remaining blocking devices, blocking device 520, blocking device 522, and blocking device 526 are left in a non-obstructing configuration. As a result, they do not reduce airflow through their respective lobar segments. Because the airflow has been reduced into the upper airway passages, air is pushed downward into the lower airway passages. As a result, the middle lobe of the right lung increases its airflow from 8% to 9%. The lower lobe of the right lung also increases its airflow—from 22% to 26%. Airflow to the lower lobe of the left lung is also increased—from 23 to 28%. Thus, the overall ventilation pattern is modified to increase the airflow to the lower lobes from 45% to 54%. With this increased airflow to the lower lobes, inhaled medications are better able to reach the areas of the lungs that are more in need of treatment. Conversely, the already healthy portions receive less treatment.

The blocking devices discussed above may be placed in various locations within the airway passages of the respiratory system. Depending on the condition of the patient, blocking devices may be placed in various locations within the airway anatomy. For example, if one lung is diseased while the other remains healthy, the blocking device may be positioned in one or both of the main bronchi in order to cause increased airflow to one lung. These blocking devices will typically be larger in size to accommodate the larger airway passages. Blocking devices may also be positioned within smaller passages such as segmental bronchi. These blocking devices are much smaller because the segmental bronchi are much narrower.

Figure 6:
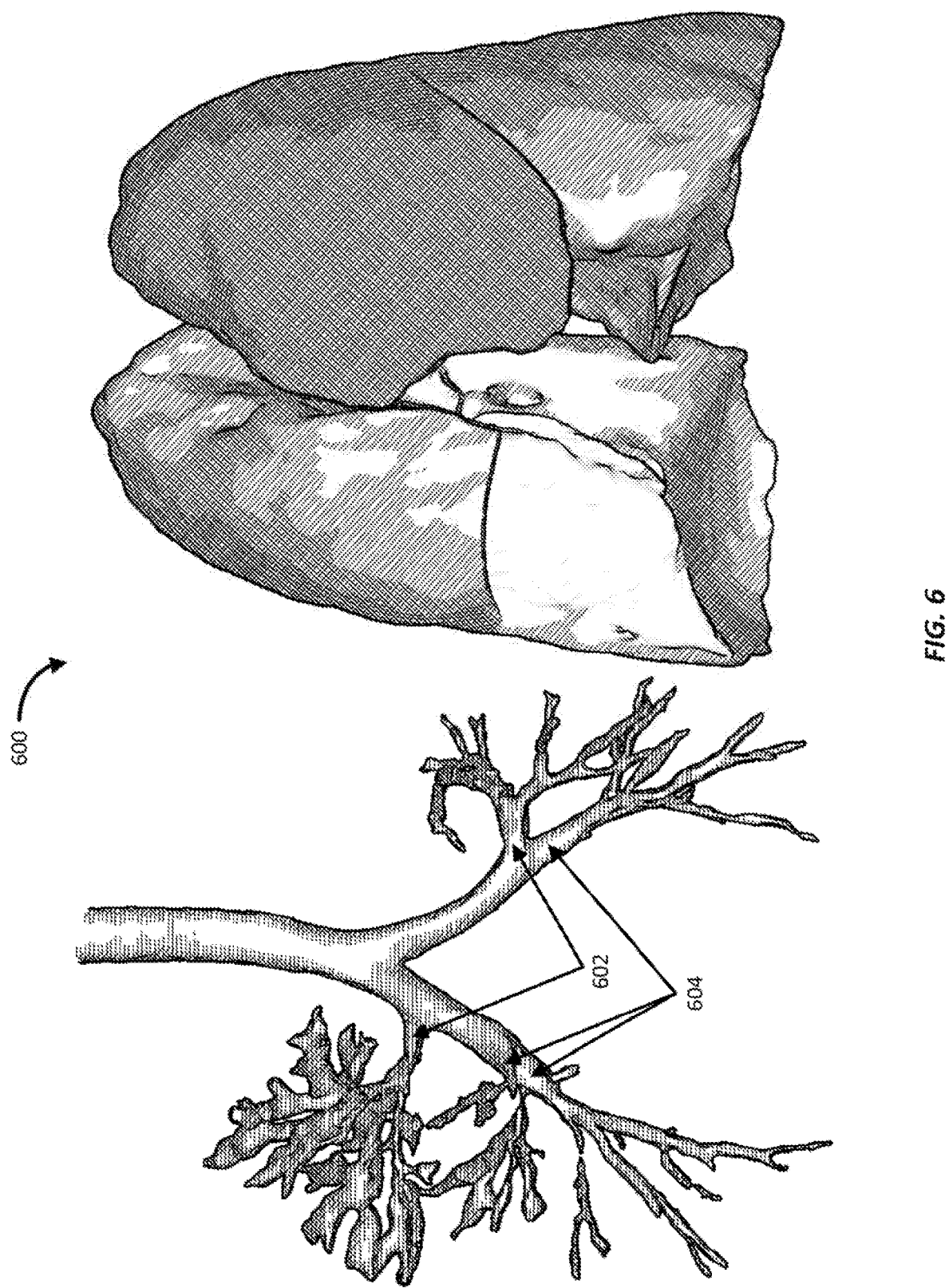
FIG. 6 provides an illustration of possible placement locations for airway obstructions according to one or more embodiments.

In the example shown above in FIG. 5C, the blocking devices were placed in the lobar bronchi. FIG. 6 provides an illustration of this particular placement. As shown, upper lung placement locations 602 are shown in the lobar bronchi leading to each of the upper lobes. Similarly, the lower airway-passage placement locations 604 are shown in the lobar bronchi leading to each of the lower lobes and the right middle lobe. Although in this particular example, the blocking devices are placed only in lobar bronchi, depending on the clinical situation, blocking devices may be placed in any combination of the main bronchi, the lobar bronchi, and the segmental bronchi.

Various different types of blocking devices may be used to obstruct airway passages within the patient's respiratory system. They may be selected in each instance based on therapeutic need, reimbursement rules, or some other selection criteria. In general, the blocking devices may take the form of airway stents which are configured to partially and/or fully block air from passing through an airway passage in which the airway stent is implanted. Various different types of airway stents may be used. In certain embodiments, off-the-shelf-stents may be used. In other embodiments, patient-specific stents may be used. FIGS. 7-10 provide examples of various different types of blocking devices which may be used in conjunction with the inventive methods described herein.

Figure 7:
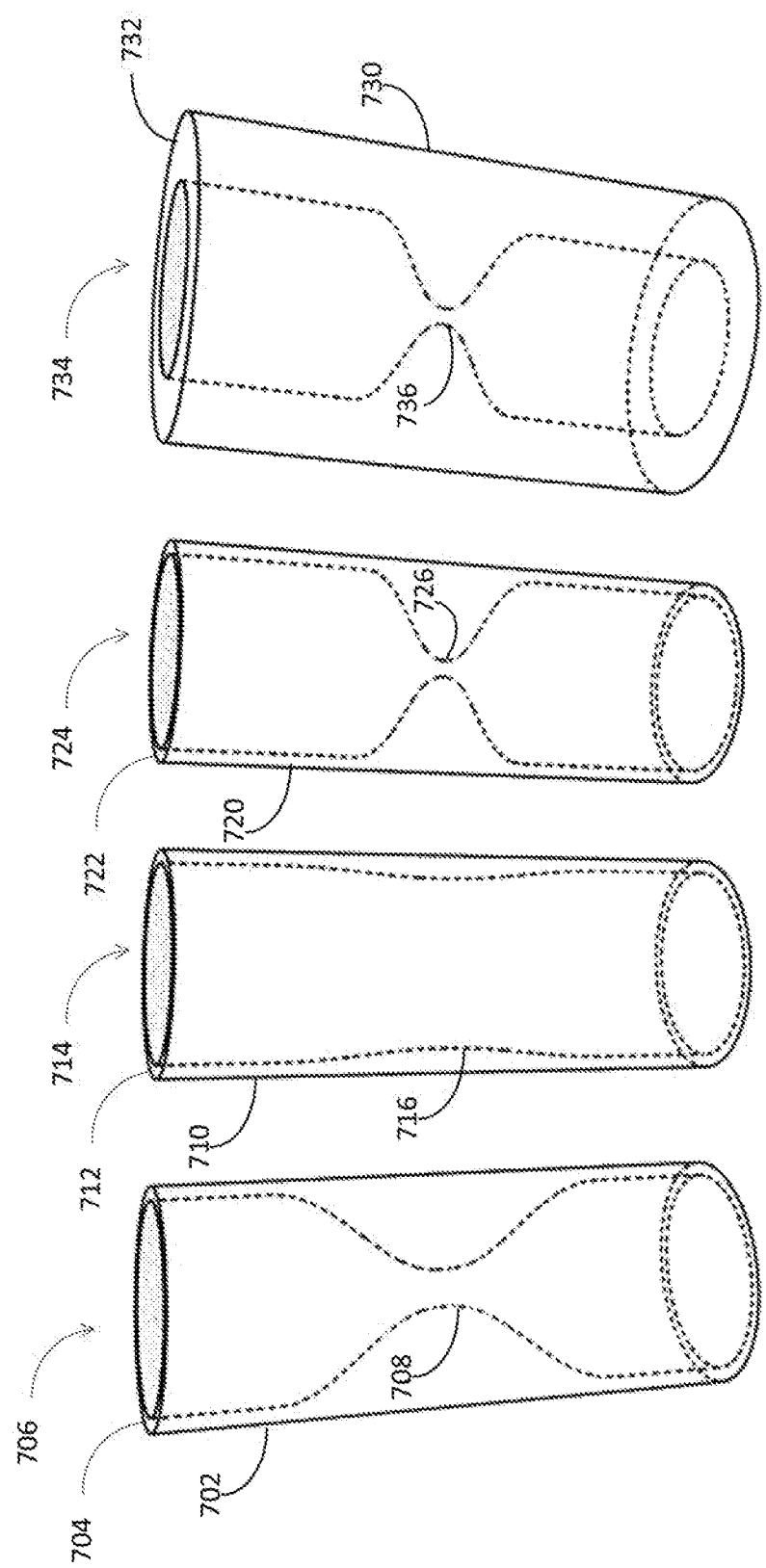
FIG. 7 provides an example of fixed off-the-shelf blocking devices that may be used to modify and/or control airflow through an airway.

FIG. 7 provides four different examples of fixed off-the-shelf bronchial stents that may be used as blocking devices which modify and/or control airflow through an airway. These four examples will be discussed starting with the left most blocking device in the figure, and proceeding right word. In some embodiments, a fixed off-the-shelf blocking device may be configured to narrow the airway passage substantially, but still allow airflow to pass through the device. Blocking device 702 is an example of such a device. Blocking device 702 may be a stent or stent-like device which is generally cylindrical in shape, and includes a smooth outer surface on the cylinder. The device 702 may be hollowed such that an outer wall 704 is formed having a thickness suitable for providing sufficient strength to the hollowed device to withstand compressive pressure placed upon it when inserted into an airway passage.

The channel 706 defined in the interior of the device 702 may have a diameter that is slightly smaller than the diameter of the device as a whole. However, the hollow tube may include a transition portion in which the size of the two becomes progressively narrower as it proceeds inward towards the center portion of the length of the cylinder. At its narrowest point 708, the inner channel creates an obstruction, which impairs the flow of air through it. In general, the outer diameter of the blocking device 702 may be close to the same diameter of the airway passage at the planned location for placement. That way, the outer diameter of the blocking device will prevent air from passing around the device along the border of the airway passage. Instead, with a reasonably snug fit, air will be directed into the hollow channel 706 where the obstructing portion can modify the airflow according to its design.

The second example shown in FIG. 7 demonstrates a fixed, off-the-shelf blocking device 710, which is configured to only slightly narrow the airway passage within which it is placed. Like the first example, the blocking device 710 is substantially cylindrical in shape, with a hollowed center which forms an outer wall 712 which provides support against external inward pressure on the blocking device 710. In this example, the hollow center 714 does not narrow sharply, but instead narrows only slightly toward an inner diameter 716, which is only slightly smaller than the diameter of the hollow tube at the ends of the blocking device 710. In this configuration, airflow will not be altered as significantly as was the case with the initial example of blocking device 702. Rather, in this particular configuration, airflow will be generally unchanged, or only slightly reduced, as the passageway is not significantly smaller than the passageway prior to insertion of the blocking device 710.

The third example shown in FIG. 7 shows a blocking device 720, which is configured to almost completely obstruct air passing through the device. As with the other two examples, the blocking device 720 includes an outer surface and an inner hollowed portion 724 which together form an outer wall 722 used to provide support to the device 720. As shown in FIG. 7, the hollow channel portion 724 extends through the cylinder and narrows at location 726 so that it is almost completely blocked. In this configuration, only a very small amount of air can pass through device 720, and the airflow within the airway passage in which this device 720 is placed will be drastically reduced.

FIG. 7 also provides a fourth example of an off-the-shelf blocking device 730. Off-the-shelf blocking device 730 provides a configuration that includes a thick outer wall 732, which may provide additional strength to the blocking device 730. A thick outer wall such as outer wall 732 may be useful for placement in airway passages susceptible to severe constriction or other movements which impose severe compressive forces on the outside of the device 730. In this particular example of the thick-walled blocking device, the inner channel 734 does not extend close to the outer diameter of the device. As a result, the wall thickness both at the ends of the cylindrical shape and toward the center are significantly larger than in prior examples. As with the other examples, the hollow channel 734 turns sharply inward in the middle portion of the blocking device 730 to form an air-passage obstruction 736. The air-passage obstruction 736 will sharply curtail the amount of air passing through the airway passage.

The examples shown in FIG. 7 each relate to blocking devices having fixed narrowing features. As such, with a blocking device placed within an airway passage, the airflow through that airway passage is partially obstructed. In some embodiments, the blocking device may not have an inner hollowed portion, or the inner hollowed portion may be completely blocked. In such embodiments, with a blocking device placed within an airway passage, the airflow through that airway passage is completely or almost completely—due to potential leakage—obstructed.

Figure 8:
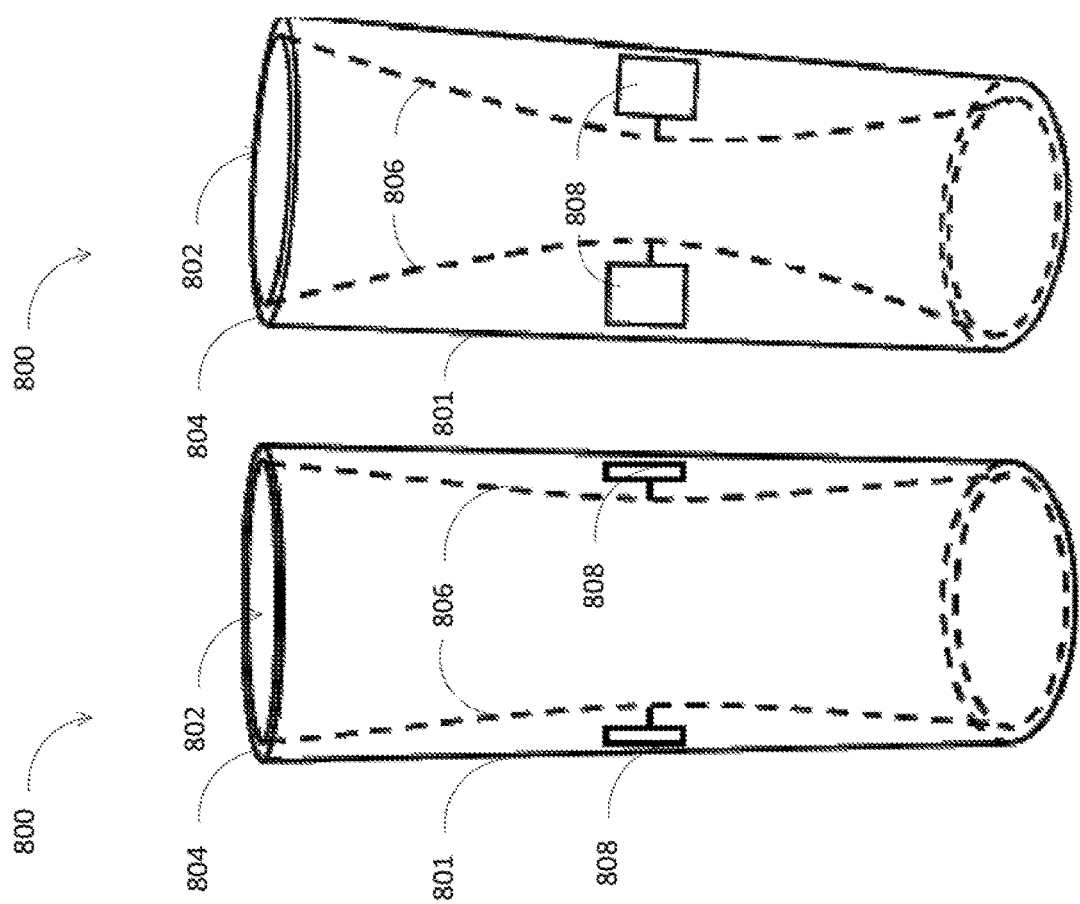
FIG. 8 provides an example of a configurable off-the-shelf blocking device that transitions to a plurality of opening and/or narrowing states.

The examples shown in FIG. 7 each relate to blocking devices having fixed narrowing features. As such, when placed within an airway passage, their modification of the airflow through that airway passage is consistent and perpetual until the blocking devices are removed from the airway passage. In some embodiments, blocking devices may be made configurable so that their obstructing properties can be modified without having to remove the device from the airway passage. FIG. 8 provides an example of a configurable off-the-shelf blocking device 800 that transitions between opening and/or narrowing states.

As shown, the configurable blocking device 800 may generally be configured in a manner similar to the off-the-shelf blocking device 700. In particular, it may include a body structure 801, which encloses a hollowed area 802 to form outer wall 804. The hollowed channel 802 may include a functional element that transitions the blocking device 800 between an open state and a narrowed state. The functional element may take the form of a microelectromechanical-systems device ("MEMS") which may be formed of one or more electrically connected movable walls 806. The movable walls 806 may be connected to electronic circuitry 808 which may be configured to receive control signals from an external stimulus and cause the walls 806 to move inward from an open state (shown in the example on the left side of the figure) toward the center of the channel 802 (as shown in the example on the right side of the figure). The electronic circuitry 808 may be powered by a battery, which is enclosed in the body structure 801 of the device 800. Electronic circuitry 808 may also be powered using other known power sources. In some embodiments, the configurable blocking device 800 may take the form of a configurable stent such as the configurable stents disclosed in U.S. Patent Pub No. 2014-0324094, the contents of which is herein incorporated by reference in its entirety.

In use, the configurable blocking device 800 may be implanted into an airway passage in an open state. Thus, while initially implanted, the configurable blocking device 800 may cause little change in the airflow through the airway passage in which it is placed. The functional element may be transitioned to a narrowed state prior to administering an inhaled drug to the patient. For example, the configurable blocking device 800 may be placed in a lobar bronchus which leads to a lobe receiving a higher than normal airflow in the measured ventilation pattern. It may be determined that this lobe receives higher than normal airflow because it is healthy, and therefore does not need treatment. When preparing to administer an inhaled drug, the functional element may be transitioned so that less air reaches this healthy portion of the lung, and more inhaled air (including the inhaled drug) is directed to the diseased portions of the lung.

Similarly, configurable stents may also be used to channel airflow toward healthy portions of the lung during those times in which treatment is not been administered. For example, configurable blocking device 800 may be placed in a lobar bronchus that extends into a diseased lobe that receives inadequate airflow during breathing. In order to increase patient comfort, airflow may be redirected away from these diseased portions by maintaining the blocking device 800 in a narrowed state. Thus, inhaled air is pushed toward the healthier portions of the lung, and the patient's breathing may be less labored and more comfortable. However, when treatment is administered, the blocking device 800 may be transitioned to an open state so that the inhaled drug reaches the diseased portion of the lung and can enhance its therapeutic effect.

Figure 9:
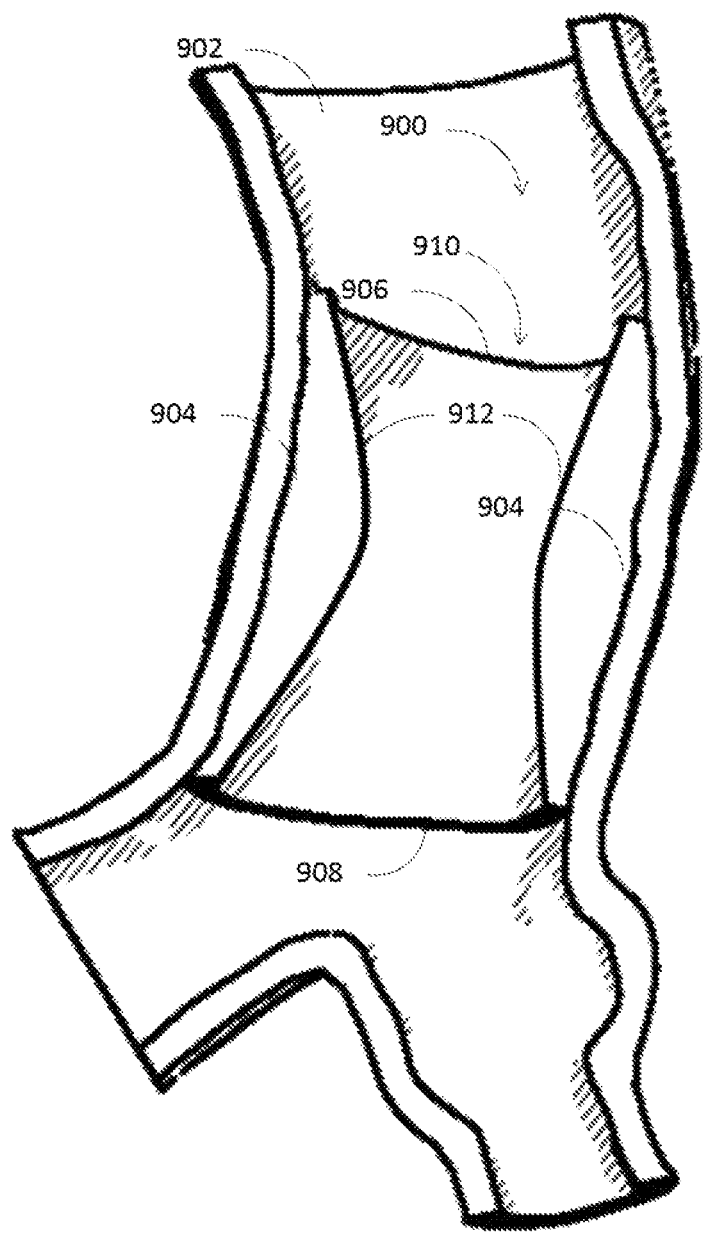
FIG. 9 is an example of a patient-specific blocking device that may be used to changeably modify airflow through an airway passage.

The blocking devices described in connection with FIGS. 7 and 8 each can be off-the-shelf devices that are configured to obstruct airways within the lungs according to the needs of the patient. In some situations, it may be desirable to use a more customized, patient-specific solution. FIG. 9 is an example of a patient-specific blocking device that may be used to changeably modify airflow through an airway passage. The patient-specific blocking device 900 may be placed within an airway passage 902. As shown, the patient-specific blocking device 900 may be formed with an exterior or outer surface 904 that conforms to the contour of the airway passage 902. By conforming to the anatomical structure of the airway passage, the outer surface 904 of the patient-specific blocking device 900 can have an improved fit within the airway passage, which can help reduce incidence of migration or movement within the airway passage. In addition, the conforming outer surface also may result in an optimal sealing of the airway, as less air is able to pass through the space between the outer wall of the device 900 and the wall of the airway passage 902. The patient specific blocking device 900 may include a free-form outer surface, which is substantially cylindrical, but shaped similarly to the inner surface of the airway passage 902.

As shown in FIG. 9, the outer surface 904 may include a proximal end 906, which is irregular in shape. The proximal end may include a channel 910, which may also be patient specific to better achieve a desired level of narrowing. The channel 910 may include interior wall 912 which may be specifically formed to achieve a patient-specific narrowing effect. The blocking device 900 may also include a distal end 908. The distal end may have an outer shape that is different from the outer shape of the proximal end 906. This is because the outer shape at the distal end may be formed to conform to the anatomical structure in the more distal location of the airway passage, while the outer shape of the proximal end 906 is formed to conform to a different, more proximal area of the airway passage. As shown, due to the snug fit, the tendency of the blocking device 900 to move within the airway passage is significantly reduced. The patient-specific blocking device 900 may be designed and manufactured using additive manufacturing technology. In some embodiments, the patient-specific blocking device 900 may be designed and manufactured using the techniques described in U.S. Pub No. 2014-0222184, the entire contents of which is hereby incorporated by reference.

In some embodiments, a direct additive manufacturing process is used to produce a patient-specific blocking device. In a direct additive manufacturing process, the end product (e.g., patient-specific blocking device), is directly printed. In some embodiments, an indirect additive manufacturing process is used to produce a patient-specific blocking device. In an indirect additive manufacturing process, a mold (e.g., mandrel) is printed and used to manufacture the end product (e.g., patient-specific blocking device). For example, a 3-D image of the anatomical structure of the airway may be obtained from the patient. A 3-D model of a mold may then be produced which conforms to the airway structure. The 3-D model of the mold may be meshed to create different segments such as tile pieces. The mold may be manufactured using an additive manufacturing device, and the manufactured mold may have a plurality of tile pieces, which are interconnected using breakable seams. The manufactured mold may be used as a mandrel, and the patient specific blocking device 900 may be manufactured using the mold. Once the patient-specific blocking device 900 has been manufactured using the mold, the mold may be removed by applying external mechanical force to it, causing the manufactured mold to break apart at the seams. In some embodiments, the patient-specific blocking device 900 may be configurable in a manner similar to the configurable blocking device 800 discussed above in connection with FIG. 8.

In some embodiments, a hybrid device, which includes some patient-specific features and some off-the-shelf and/or non-customized features, may be used. In particular, a patient-specific docking station may be manufactured to conform to the patient anatomy of the airway in which it is to be placed, and also to receive a functional element that controls and/or obstructs the passage of air through the device. The docking station can include a body structure having an outer surface that conforms to the anatomy of the placement location. The body structure may also include an inner surface that has docking features that are configured to engage the functional element to hold the functional element in place within the body structure. The functional element may be replaceable using a non-surgical interventional approach. Moreover, the functional element may be a configurable device that allows for transitioning between an open and a narrowed state.

Figure 10:
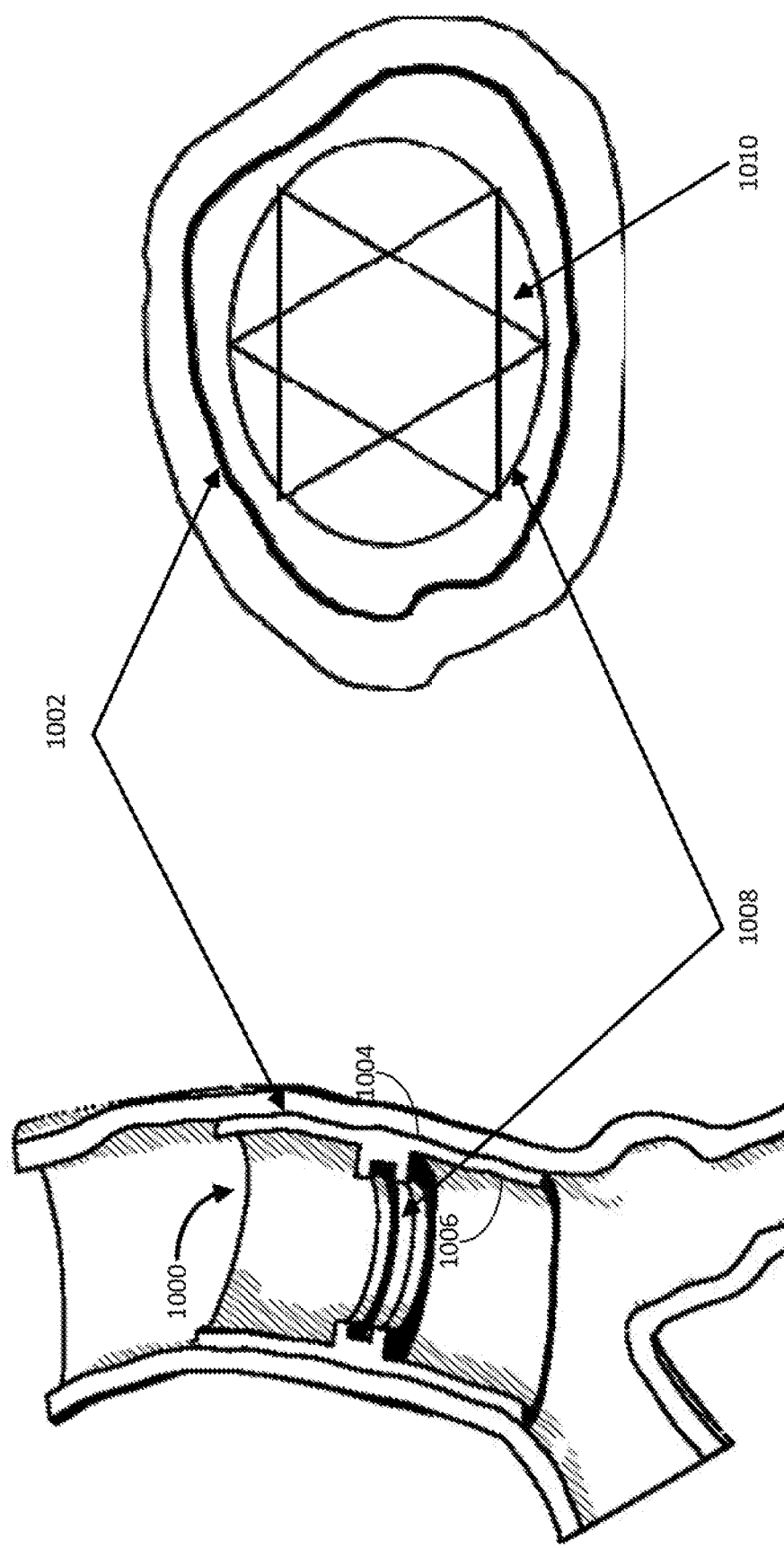
FIG. 10 provides an example of a hybrid blocking device which uses a docking station and a replaceable blocking element.

FIG. 10 shows an example of a hybrid device 1000, which may be used in accordance with one or more embodiments. In particular, FIG. 10 provides an example of a hybrid blocking device 1000, which uses a patient-specific docking station and a replaceable blocking element. The hybrid blocking device 1000 includes an outer surface 1002 that is generally conforming to the inner surface 1004 of an airway passage in which it has been positioned. As shown, the hybrid blocking device 1000 also includes an inner surface 1006 having docking features 1008 which are configured to receive functional element 1010. Functional element 1010 may include a fixed or configurable narrowing of its inner diameter, which allows for control of airflow through the airway passage. The functional element 1010 may be replaceable in such a way that it can be exchanged for a different functional element with different obstructing properties while administering treatment to a patient. In addition, the functional element 1010 may take the form of a drug-delivery system, such as a drug-eluting device or a nebulizer, which can be placed in the airway passage for a period of time, and then removed when the drug-delivery process is complete. In some embodiments, the administered drugs may comprise vasodilators. In some embodiments, the hybrid device may be similar to the devices disclosed in U.S. Patent Pub. No. 2014-0088698, the entire contents of which is hereby incorporated by reference.

Figure 11:
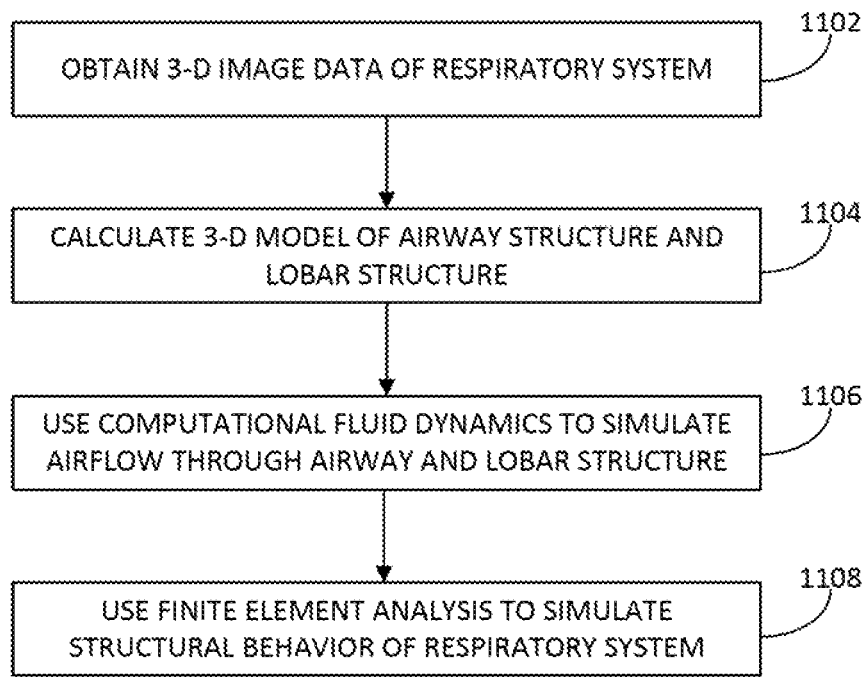
FIG. 11 is a flow chart showing one example of a process for determining airflow within a patient's lung.

The various blocking devices described above may be used to modify airflow through airway passages of a patient's respiratory system. As noted above, airflow or ventilation pattern may be modeled using various techniques, including functional respiratory imaging ("FRI"). FIG. 11 is a flow chart showing a high-level process for performing FRI to determine airflow within a patient's lung. The process begins at block 1102, where 3-D image data of a patient's respiratory system is obtained using an imaging device. The imaging device may be any known imaging device, including MRI, CT, ultrasound, or other type of imaging device. Once the 3-D image data has been obtained, the process moves to block 1104. There, a 3-D model of the airway structure and lobar structure is calculated and produced. The process then moves to block 1106 where computational fluid dynamics are used to simulate airflow through the airway and lobar structure. The process then moves to block 1108, where finite element analysis is used to simulate the structural behavior of the respiratory system as air passes through it. In modeling airflow within the respiratory system, FRI techniques may be used such as those described in U.S. Pat. No. 8,886,500, the entire contents of which is hereby incorporated by reference.

Figure 12:
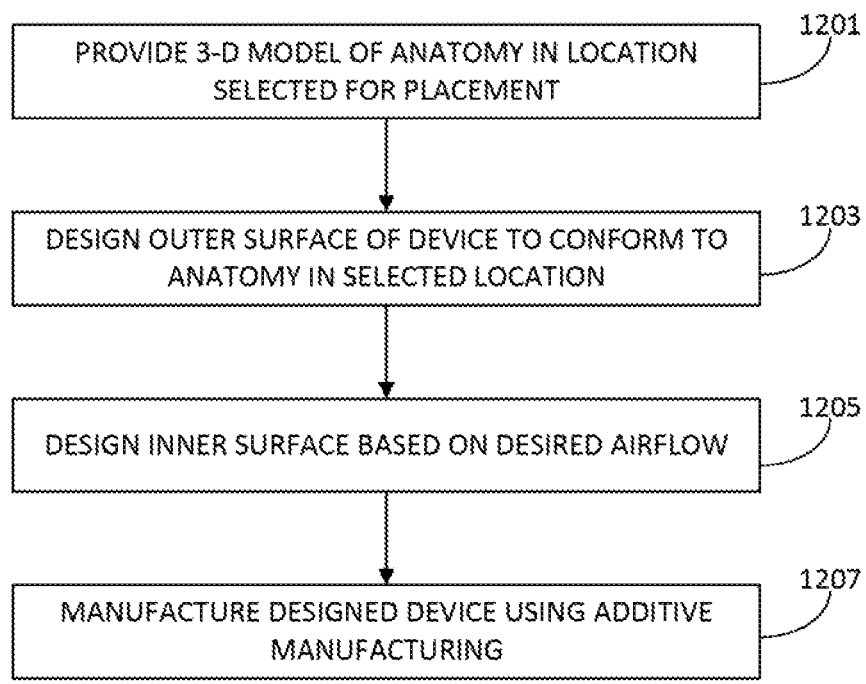
FIG. 12 is a flow chart showing an example of a process for creating a patient-specific blocking device such as the blocking device shown in FIG. 9.

As noted above, patient-specific blocking devices may be manufactured and utilized in accordance with various embodiments disclosed herein. FIG. 12 is a flow diagram of an example process for creating a patient-specific blocking device such as the blocking device 900 shown in FIG. 9. The manufacturing process begins at block 1201, where a 3-D model of the anatomical structure of the airway is provided. In particular, the selected location for placement of the patient-specific blocking device may be obtained and provided to 3-D design and modeling software. Next, the process moves to block 1203, where the outer surface of the patient-specific device is designed such that it conforms to the anatomy in the selected location. Thus, the outer surface of the patient-specific device may be designed to be substantially similar in shape to the inner walls of the airway passage in which it is to be placed. Next, the process moves to block 1205 where the inner surface of the patient-specific blocking device is designed. The inner surface may be designed based on the desired airflow which has been determined based on the FRI or other simulation process described above in connection with FIG. 11. Once the inner surface has been designed with the appropriate narrowing feature, the process moves to block 1207. There the designed device may be manufactured using additive manufacturing technologies.

Figure 13:
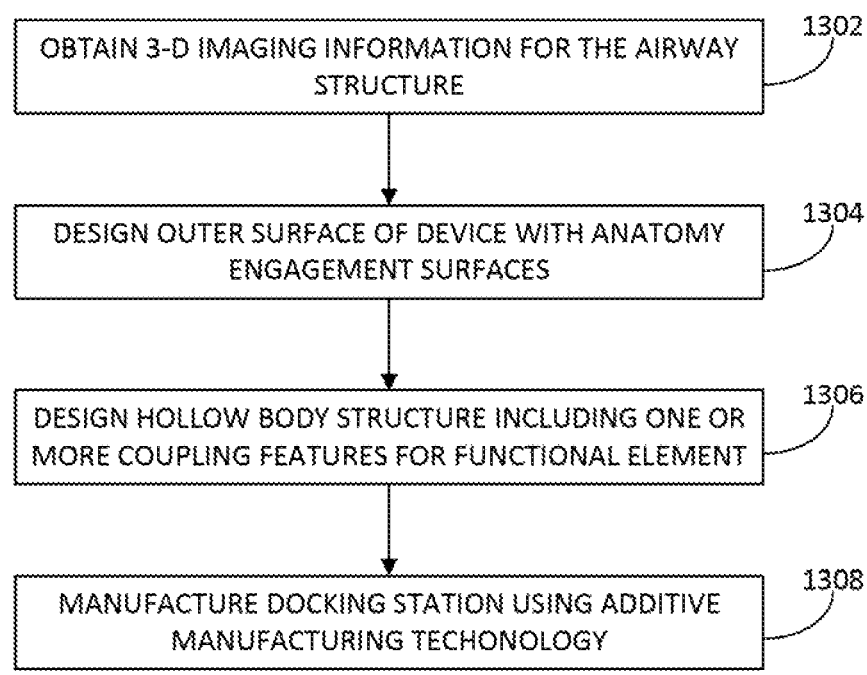
FIG. 13 is a flow chart showing an example of a process for creating a patient-specific docking station.

The patient-specific docking-station device described above in connection with FIG. 10 may also be produced using a similar process. Turning now to FIG. 13, a flow diagram for an example process of creating a patient-specific docking station is provided. The process begins at block 1302 where 3-D imaging information for the airway structures is obtained. Next, the process moves to block 1304 where the outer surface of the docking station is designed to include anatomy-engagement surfaces. The process continues at block 1306 where the hollow body structure including one or more coupling features for a functional element are provided. Next, the process moves to block 1308 in which the docking station may be manufactured using additive manufacturing technology.

Figure 14:
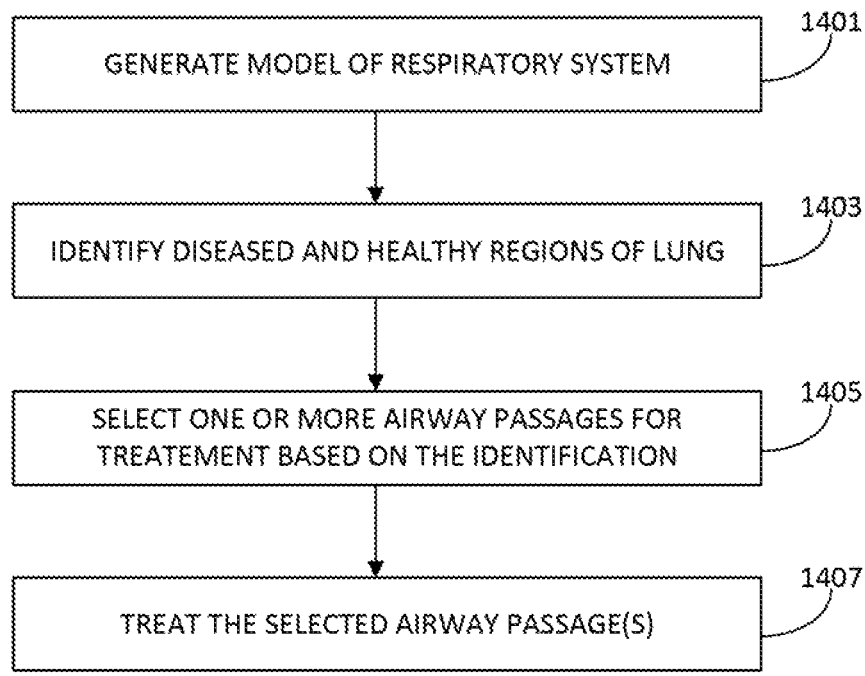
FIGS. 14-18 are flow charts depicting various methods of treating a respiratory condition in a patient according to various embodiments.

FIGS. 14-18 are flow charts depicting various methods of treating a respiratory condition in a patient using the techniques and devices discussed above. FIG. 14 depicts a general method for treating a respiratory condition in a patient according to one or more embodiments of the invention. As shown, the process begins at block 1401, where a model of the respiratory system is created and/or generated. As discussed above, the model of the respiratory system may be created using various modeling techniques, including functional-respiratory-imaging techniques described in U.S. Pat. No. 8,886,500. Next, using the model, diseased and healthy regions of the lungs may then be identified at block 1403. In some embodiments, this identification is based on abnormalities in the airflow shown in the generated model. In other situations, medical imaging may also be used to observe disease within certain regions of the lung. Next, the process moves to block 1405 where one or more airway passages are selected for treatment based on the identification of healthy and diseased regions of the lung. Once the airway passages have been selected, they are then treated at block 1407. Treatment of the lungs as described in block 1407 may involve the use of blocking devices such as those described above in connection with FIGS. 7-10.

Figure 15:
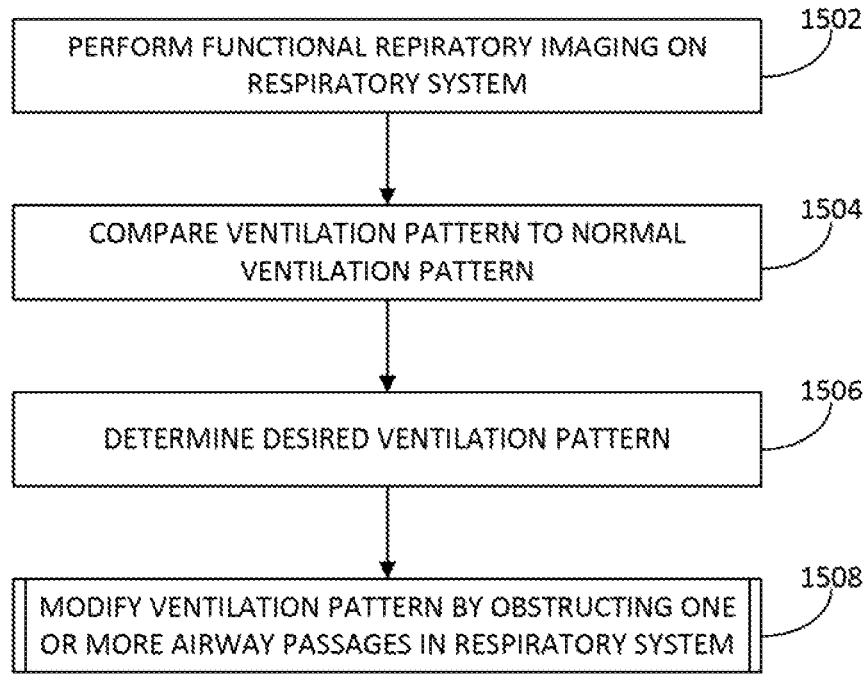

FIG. 15 is a flow chart that shows a more detailed process for treating a respiratory condition in a patient. This process begins at block 1502 where functional respiratory imaging is performed on the respiratory system of the patient. The process then moves to block 1504. There, the ventilation pattern observed in the FRI process is compared to a normal ventilation pattern. For example, the measured ventilation pattern may be preferential towards upper lobes due to disease in the middle and lower lobes of the lungs, such as the disease shown in FIGS. 2-3 above. The process then moves to block 1506 where a desired ventilation pattern is determined and/or identified for the patient. Once the desired ventilation pattern has been determined, the process moves to block 1508 where the ventilation pattern is modified by obstructing one or more airway passages in the respiratory system.

Figure 16:
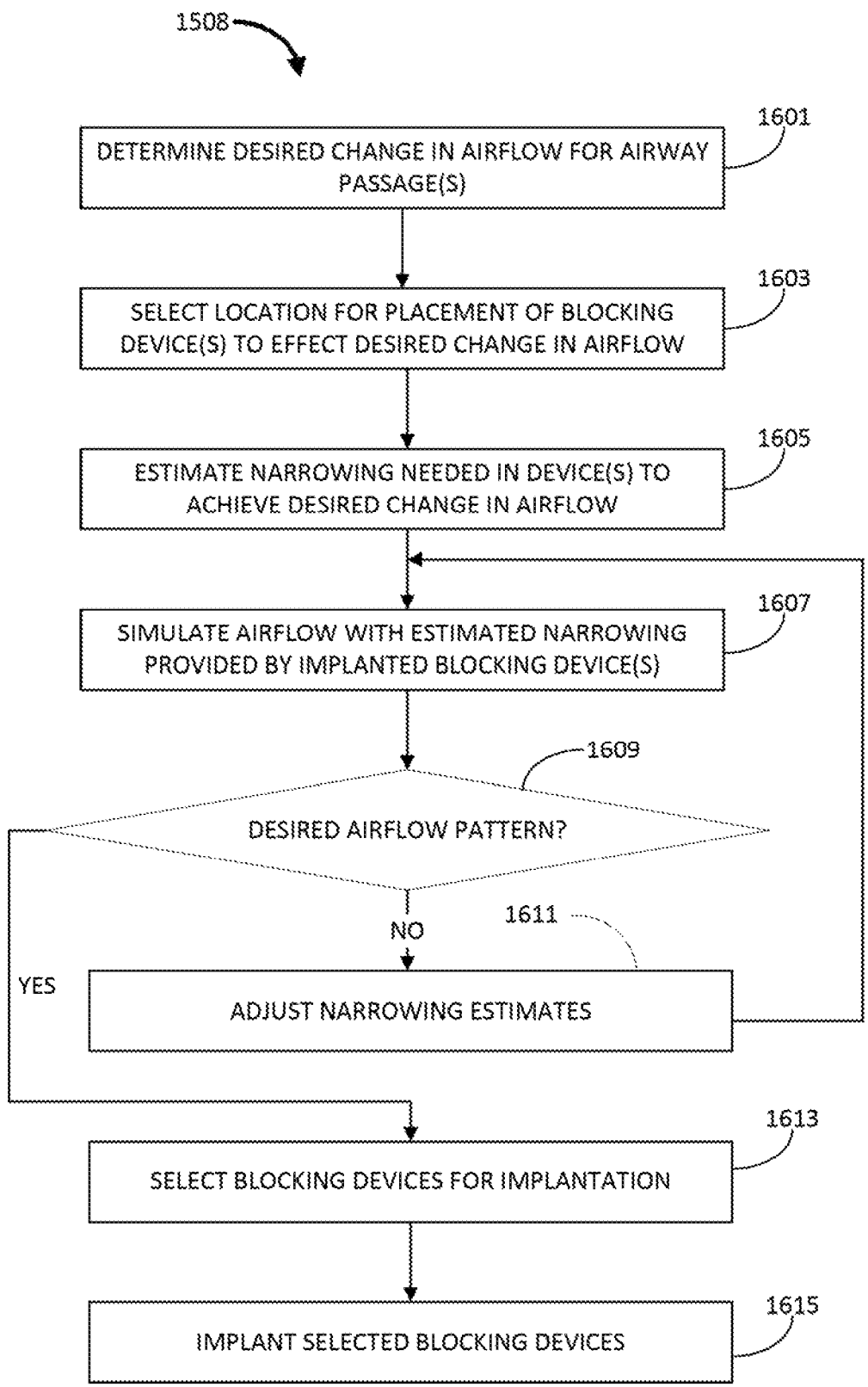

FIG. 16 is a sub-process of the ventilation-pattern-modification step shown in block 1508 of FIG. 15. This process begins at block 1601, where the desired change in airflow for one or more airway passages is determined. For example, the desired change may involve reducing airflow to the healthy lung areas while increasing airflow to diseased lung areas in order to more effectively deliver inhaled medication. The process then continues to block 1603, where the location (or locations) for placement of a blocking device (or blocking devices) is selected. In many of the examples described above, these locations typically were within a lobar bronchus of the lung. However, it is to be appreciated that these locations may also include segmental bronchi, or larger airway passages such as the trachea and/or main bronchus. Next, the process moves to block 1605. There, the amount of narrowing needed to effectuate the desired change in airflow in the blocking devices is estimated. These estimates may be based on the knowledge and experience of the treating physician, or they may be computer-generated using mathematical algorithms that can model implant behavior.

Next, the process moves to block 1607 where airflow is simulated in the respiratory system after placement of the blocking devices with the estimated narrowing. The simulation results are reviewed to determine whether the initial configuration provides a desired airflow pattern at decision step 1609. If not, the process moves to block 1611 where the amount of narrowing in the implanted blocking devices is adjusted. Then, the process returns to block 1607 where the simulation is performed once again. This loop continues until a desired airflow pattern is reached at decision block 1609. When the desired airflow pattern is reached, the process advances to block 1613. There, the appropriate blocking devices having the appropriate amount of narrowing are selected for use. The process then continues to block 1615 where the selected blocking devices are implanted in the airway passages of the patient.

Figure 17:
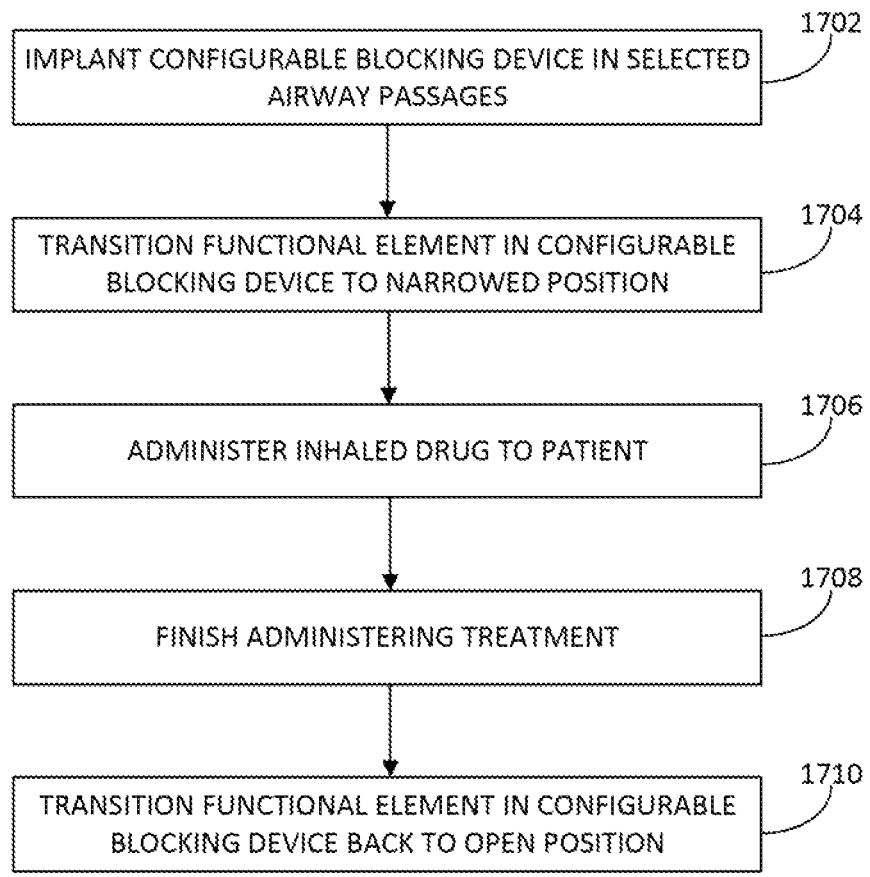

FIG. 17 is a flow chart providing an example of how the configurable blocking device may be used according to one or more embodiments. The process begins at block 1702, where the configurable blocking device is implanted or placed in selected airway passages. The process continues to block 1704 where the functional element in the configurable blocking device is transitioned to a narrowed position. Once the functional element has been transitioned, an inhaled drug may be administered to the patient at block 1706. At block 1708, the administration of treatment is completed. Because the administration of treatment is completed, there is no longer a need for the blocking device to be in a narrowed state. As a result, at block 1710, the functional element in the configurable blocking device is transitioned back to an open state or position.

Figure 18:
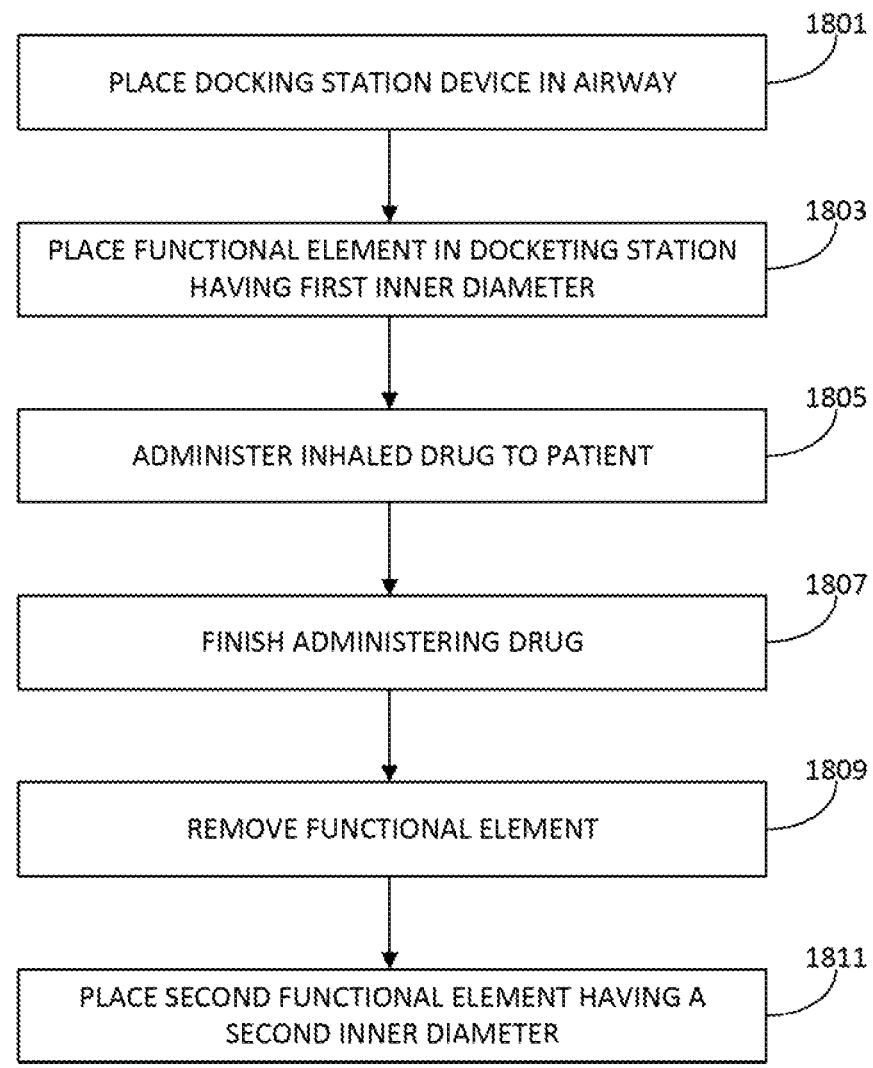

Turning now to FIG. 18, the process for using a hybrid blocking device for treating a respiratory condition in a patient is provided. The process begins at block 1801, where the hybrid device, which may be a docking-station device, is placed in an airway of the patient. Next, at block 1803, the functional element having a first inner diameter is placed within the docking station. At block 1805, the process continues with an inhaled drug being administered to the patient. At block 1807, the administration of the drug is completed and the process continues to block 1809. There the functional element is removed from the docking station. Next, the process moves to block 1811 where a second functional element having a second inner diameter is placed within the docking station. It is to be appreciated that any number of different functional elements having any number of different diameters may be placed within the docking station depending on the therapeutic need.

The present invention also provides for methods in which the progress of the healing process is monitored over time. This progress can be assessed by repeating the FRI step after a predetermined period of time, and comparing the information provided by the simulation with the information obtained before the initial treatment. The comparison may indicate that additional treatment is warranted.

Several devices described above may be manufactured using additive manufacturing techniques. Additive manufacturing is particularly useful for the manufacture of hollow objects. The material used to manufacture the blocking devices may depend on the (additive) manufacturing method used and the specifications of the blocking device to be manufactured. In particular embodiments, the blocking devices may be made of material that is compatible with additive manufacturing, including polymeric materials, metals, metal alloys, ceramic materials and glass. In some embodiments, the blocking device may be made of one or more of polyamide, polystyrene, polyurethane, steel, titanium, or aluminum. The blocking devices disclosed herein may also be made of a composite material, such as glass-filled polyamide or alumide. Alumide is a blend of polyamide and aluminum powder.

Aspects of the disclosed embodiments may be performed by computing devices. These computing devices may be general-purpose computers or special-purpose computers which include processors configured to read and execute instructions from a non-transitory computer-readable medium. More particularly, it is provided in a data-processing apparatus or system which comprises means for carrying out the method as described herein, in a computer program adapted to perform the different steps of the method as provided herein carried on an electrical carrier signal or a computer program comprising software code adapted to perform the method as described herein. The data-processing system or computer program as provided herein particularly refer to computer-aided design and manufacturing systems and programs such as CAD/CAM systems or programs.

What is claimed is:

1. A method of controlling airflow distribution in a lung of a respiratory system of a patient, the method comprising:

obtaining, at a computing device, a 3-D model of at least part of the respiratory system;

performing, by the computing device, computational fluid dynamics simulation on the 3-D model to generate a first computer model of airflow through the at least part of the respiratory system;

identifying at least one diseased region of the lung based on the first computer model indicating the at least one diseased region of the lung has a reduced airflow as compared to a threshold healthy airflow for the at least one diseased region;

identifying at least one healthy region of the lung based on the first computer model indicating the at least one healthy region of the lung has at least a threshold healthy airflow for the at least one healthy region;

selecting, based on the first computer model and the identified at least one healthy region of the lung, at least one airway passage to the at least one healthy region;

placing at least one device in the at least one airway passage to the at least one healthy region, the at least one device having a channel;

based on the at least one diseased region of the lung, determining a level of narrowing of the channel for the at least one device for the at least one airway passage; and administering a powder form inhaled drug to the lung by inhalation of the inhaled drug by the patient via a mouth or nose of the patient while the channel of the at least one device is configured to be at the determined level of narrowing that is narrower than the at least one airway passage to reduce airflow through the at least one airway passage to the at least one healthy region thereby increasing airflow to the at least one diseased region.

2. The method of claim 1, wherein performing the computational fluid dynamics simulation on the 3-D model comprises:

modeling a structural behavior of the at least part of the respiratory system; and modeling an interaction of the structural behavior with the airflow through the at least part of the respiratory system.

3. The method of claim 1, wherein the first computer model determines at least one or more of airway volumes, lobe volumes, airway resistance, lobar ventilation, perfusion, and particle deposition.

4. The method of claim 1, wherein performing the computational fluid dynamics simulation on the 3-D model comprises simulating particle deposition.

5. The method of claim 1, further comprising determining an optimal ventilation-perfusion ratio.

6. The method of claim 1, wherein the at least one device comprises a body structure and a functional structure with one or more walls.

7. The method of claim 6, wherein the body structure comprises an inner surface, comprising one or more docking structures configured to detachably engage with the functional structure, wherein the one or more docking structures are configured to engage the functional structure to hold it stable within an interior of the body structure.

8. The method of claim 7, wherein the functional structure can be placed and removed with a non-surgical interventional approach.

9. The method of claim 7, wherein the inner surface is one of circular, ellipsoid and polygonal in shape.

10. The method of claim 7, wherein the functional structure has an inner diameter determining a level of narrowing of the channel for the at least one device for the at least one airway passage.

11. The method of claim 10, further comprising:
placing the functional structure in the body structure prior to the administering the inhaled drug to the lung; and
removing the functional structure from the body structure after the administering the inhaled drug to the lung.

12. The method of claim 10, further comprising:
removing the functional structure, having the inner diameter, from the body structure, prior to the administering the inhaled drug to the patient; and
placing a second functional element, having a second inner diameter, in the body structure, prior to the administering the inhaled drug to the patient.

13. The method of claim 12, wherein the inner diameter is greater than the second inner diameter.

14. The method of claim 12, further comprising removing the second functional element from the body structure and placing the functional element in the body structure after the administering the inhaled drug to the patient.

15. The method of claim 6, wherein the at least one device is a configurable device, and wherein the one or more walls of the functional structure are configured to transition between an open state and a narrowed state.

16. The method of claim 15, wherein the transition between the open state and the narrowed state is in response to an external stimulus.

17. The method of claim 15, further comprising
transitioning the functional element to one of the open state and the narrowed state prior to the administering the inhaled drug to the patient; and
transitioning the functional element to another one of the open state and the narrowed state after the administering the inhaled drug to the patient.

18. The method of claim 6, wherein the body structure comprises an outer surface comprising one or more anatomy-engagement surfaces or contact points that conform to a contour of the at least one airway passage.

19. The method of claim 6, further comprising based on the level of narrowing of the channel for the at least one device for the at least one airway passage, adjusting a position of the one or more walls of the functional structure.

20. The method of claim 6, further comprising manufacturing at least part of the at least one device, wherein manufacturing at least part of the at least one device comprises manufacturing at least part of the at least one device using at least one of direct additive manufacturing or indirect additive manufacturing.

21. The method of claim 6, further comprising selecting the at least one device from a library of devices of different shapes and/or sizes, wherein selecting the at least one device from the library of devices of different shapes and/or sizes is based on at least one dimension of the at least one airway passage.

22. The method of claim 6, further comprising selecting the at least one device from a library of devices of different shapes and/or sizes; and
wherein selecting the at least one device from the library of devices of different shapes and/or sizes is based on the determined level of narrowing of the channel for the at least one device for the at least one airway passage.

23. The method of claim 1, wherein the at least one device is one of a stent, a splint, a graft or a valve.

24. The method of claim 1, wherein the at least one device is a configurable device configured to transition between an open state and a narrowed state, wherein the open state is configured to maintain airflow in the at least one airway passage.

\* \* \* \* \*